(12) United States Patent
Daines et al.

(10) Patent No.: US 7,109,213 B2
(45) Date of Patent: Sep. 19, 2006

(54) AMINOPIPERIDINE COMPOUNDS, PROCESS FOR THEIR PREPARATION, AND PHARMACEUTICAL COMPOSITIONS CONTAINING THEM

(75) Inventors: Robert A Daines, Collegeville, PA (US); William Henry Miller, Collegeville, PA (US); Neil David Pearson, Harlow (GB); Israil Pendrak, Collegeville, PA (US); Mark Andrew Seefeld, Collegeville, PA (US)

(73) Assignee: Glaxo Group Limited, Greenford (GB)

( * ) Notice: Subject to any disclaimer, the term of this patent is extended or adjusted under 35 U.S.C. 154(b) by 0 days.

(21) Appl. No.: 10/502,234

(22) PCT Filed: Jan. 27, 2003

(86) PCT No.: PCT/EP03/00824

§ 371 (c)(1),
(2), (4) Date: Jul. 22, 2004

(87) PCT Pub. No.: WO03/064431

PCT Pub. Date: Aug. 7, 2003

(65) Prior Publication Data

US 2005/0085494 A1    Apr. 21, 2005

(30) Foreign Application Priority Data

Jan. 29, 2002  (GB) .................................. 0202025.3
Dec. 20, 2002  (GB) .................................. 0229819.8

(51) Int. Cl.
*C07D 471/02* (2006.01)
*C07D 215/16* (2006.01)
*A61K 31/44* (2006.01)
*A61K 31/47* (2006.01)

(52) U.S. Cl. ...................... 514/312; 313/314; 313/300; 546/122; 546/153; 546/159

(58) Field of Classification Search ................ 514/312, 514/313, 314, 300; 546/122, 153, 159
See application file for complete search history.

(56) References Cited

U.S. PATENT DOCUMENTS

| | | |
|---|---|---|
| 5,264,431 A | 11/1993 | Wacker et al. |
| 6,403,610 B1 | 6/2002 | Malleron et al. |
| 6,602,882 B1 | 8/2003 | Davies et al. |
| 6,602,884 B1 | 8/2003 | Bacque et al. |
| 6,603,005 B1 | 8/2003 | Baque et al. |
| 6,803,369 B1 | 10/2004 | Erskine et al. |
| 6,815,547 B1 | 11/2004 | Bacque et al. |
| 6,841,562 B1 | 1/2005 | Bacque et al. |
| 6,903,217 B1 | 6/2005 | Bacque et al. |
| 6,911,442 B1 | 6/2005 | Davies et al. |
| 6,962,917 B1 | 11/2005 | Davies et al. |
| 6,989,447 B1 | 1/2006 | Markwell et al. |
| 7,001,913 B1 | 2/2006 | Davies et al. |
| 2003/0203917 A1 | 10/2003 | Erskine et al. |
| 2003/0212084 A1 | 11/2003 | Hatton et al. |
| 2004/0053928 A1 | 3/2004 | Davies et al. |
| 2004/0077655 A1 | 4/2004 | Dartois et al. |
| 2004/0077656 A1 | 4/2004 | Markwell et al. |
| 2004/0087619 A1 | 5/2004 | Bacque et al. |
| 2004/0138219 A1 | 7/2004 | Davies et al. |
| 2004/0171620 A1 | 9/2004 | Brooks et al. |
| 2004/0198755 A1 | 10/2004 | Dartois et al. |
| 2004/0198756 A1 | 10/2004 | Davies et al. |
| 2005/0159411 A1 | 7/2005 | Daines et al. |
| 2006/0014749 A1 | 1/2006 | Davies et al. |
| 2006/0040925 A1 | 2/2006 | Davies et al. |
| 2006/0041123 A1 | 2/2006 | Axten et al. |

FOREIGN PATENT DOCUMENTS

| | | |
|---|---|---|
| BE | 772190 A1 | 1/1972 |
| CA | 2004986 A1 | 6/1990 |
| CA | 2500320 A1 | 4/2004 |
| EP | 0238868 A2 | 9/1987 |
| EP | 0304493 A1 | 3/1989 |
| EP | 0374095 A2 | 6/1990 |
| EP | 0541486 A1 | 5/1993 |
| EP | 0823429 A1 | 2/1998 |
| EP | 1218370 B1 | 12/2004 |
| GB | 1345872 | 2/1974 |
| GB | 1537867 | 1/1979 |
| JP | 1995179407 A | 7/1995 |
| WO | WO 95/09853 | 4/1995 |
| WO | WO 96/15128 | 5/1996 |
| WO | WO 97/03069 | 1/1997 |
| WO | WO 97/17957 | 5/1997 |
| WO | WO 97/28167 | 8/1997 |
| WO | WO 98/02438 | 1/1998 |
| WO | WO 99/37635 | 7/1999 |
| WO | WO 00/21948 | 4/2000 |
| WO | WO 00/21952 | 4/2000 |
| WO | WO 00/43383 | 7/2000 |
| WO | WO 00/78748 | 12/2000 |

(Continued)

OTHER PUBLICATIONS

U.S. Appl. No. 09/600,984, Coates et al., filed Jan. 21, 1999, Quinoline Derivatives as Anti-bacterials, WO99/37635.

(Continued)

*Primary Examiner*—D. Margaret Seaman
(74) *Attorney, Agent, or Firm*—Loretta Sauermelch; Mary McCarthy; Charles Kinzig

(57) ABSTRACT

Aminopiperidine derivatives and pharmaceutically acceptable derivatives thereof useful in methods of treatment of bacterial infections in mammals, particularly in man.

16 Claims, No Drawings

FOREIGN PATENT DOCUMENTS

| WO | WO 01/07432 | | 2/2001 |
|---|---|---|---|
| WO | WO 01/07433 | | 2/2001 |
| WO | WO 01/25227 | A2 | 4/2001 |
| WO | WO 01/87839 | A1 | 11/2001 |
| WO | WO 02/08224 | | 1/2002 |
| WO | WO 02/082241 | A1 * | 1/2002 |
| WO | WO 02/24684 | | 3/2002 |
| WO | WO 02/40474 | A2 | 5/2002 |
| WO | WO 02/50040 | A1 | 6/2002 |
| WO | WO 02/50061 | A1 | 6/2002 |
| WO | WO 02/056882 | | 7/2002 |
| WO | WO 02/056882 | A1 | 7/2002 |
| WO | WO 02/072572 | A1 | 9/2002 |
| WO | WO 02/096907 | A1 | 12/2002 |
| WO | WO 03/010138 | A2 | 2/2003 |
| WO | WO 03/064421 | A1 | 8/2003 |
| WO | WO 03/087098 | A1 | 10/2003 |
| WO | WO 04/002490 | A2 | 1/2004 |
| WO | WO 04/002992 | A1 | 1/2004 |
| WO | WO 04/014361 | A1 | 2/2004 |
| WO | WO 04/024712 | A1 | 3/2004 |
| WO | WO 04/024713 | A1 | 3/2004 |
| WO | WO 04/035569 | A2 | 4/2004 |
| WO | WO 04/041210 | A2 | 5/2004 |
| WO | WO 04/050036 | A2 | 6/2004 |
| WO | WO 04/058144 | A2 | 7/2004 |
| WO | WO 04/096982 | A2 | 11/2004 |

OTHER PUBLICATIONS

U.S. Appl. No. 09/889,820, Davies et al., filed Jan. 17, 2000, Quinoline Derivatives Antibacterials, WO00/43383.

U.S. Appl. No. 11/292,011, Davies et al., filed Dec. 1, 2005, Aminopiperidine Derivatives as Antibacterials.

U.S. Appl. No. 10/518,656, Axten et al., filed Jun. 25, 2003, Compounds, WO04/002992.

U.S. Appl. No. 10/518,655, Axten et al., filed Jun. 25, 2003, Compounds, WO04/002490.

U.S. Appl. No. 10/868,315, cont of 09/912,610, Erskine et al., filed Jun. 15, 2004, Compounds and Methods for the Treatment of Disease.

U.S. Appl. No. 10/199,933, CIP of 09/912,610, Erskine et al., Jul. 19, 2002, Compounds andethods for the Treatment of Disease.

U.S. Appl. No. 10/937,468, CIP of 09/912,610, Erskine et al., Sep. 9, 2004, Compounds and Methods for the Treatment of Disease.

U.S. Appl. No. 10/533,501, Axten et al., filed Nov. 4, 2003, Antibacterial Agents, WO04/041210.

U.S. Appl. No. 10/533,502, Axten et al., filed Nov. 4, 2003, Antibacterial Agents, WO04/096982.

U.S. Appl. No. 10/537,034, Axten et al., Dec. 3, 2003, Quinolines and Nitrogenated Derivatives thereof and their Use as Antibacterial Agents, WO04/050036.

* cited by examiner

AMINOPIPERIDINE COMPOUNDS, PROCESS FOR THEIR PREPARATION, AND PHARMACEUTICAL COMPOSITIONS CONTAINING THEM

This invention relates to novel compounds, compositions containing them and their use as antibacterials.

WO99/37635, WO00/21948, WO00/21952, WO01/25227, WO00/43383, WO00/78748, WO01/07432 and WO01/07433 disclose piperidine and piperazine derivatives having antibacterial activity.

WO9717957 discloses piperidyl compounds which are haemoregulatory and stimulate haematopoesis. JP07179407 discloses piperidyl compounds which are useful for preventing thrombotic diseases, inhibiting tumour metastasis and accelerating wound healing.

We have now found a novel group of aminopiperidines which have antibacterial activity.

This invention provides a compound of formula (I) or a pharmaceutically acceptable derivative thereof:

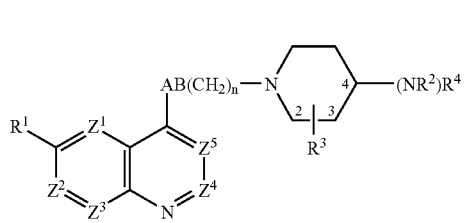

(I)

wherein:
one of $Z^1$, $Z^2$, $Z^3$, $Z^4$ and $Z^5$ is N, one is $CR^{1a}$ and the remainder are CH, or one or two of $Z^1$, $Z^2$, $Z^3$, $Z^4$ and $Z^5$ are independently $CR^{1a}$ and the remainder are CH;

$R^1$ and $R^{1a}$ are independently hydrogen; hydroxy; $(C_{1-6})$alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted$(C_{1-6})$alkyl; halogen; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups;

or when $Z^5$ is $CR^{1a}$, $R^{1a}$ may instead be cyano, hydroxymethyl or carboxy;

or $R^1$ and $R^{1a}$ on adjacent positions may together form ethylenedioxy;

provided that when $Z^1$, $Z^2$, $Z^3$, $Z^4$ and $Z^5$ are $CR^{1a}$ or CH, then $R^1$ is not hydrogen;

$R^2$ is hydrogen, or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkoxycarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenylsulphonyl; $(C_{2-4})$alkenylcarbonyl; oxo or $(C_{1-4})$aminosulphonyl wherein the amino group is optionally substituted by $(C_{1-4})$alkyl or $(C_{2-4})$alkenyl;

$R^3$ is in the 2-, 3- or 4-position and is trifluoromethyl or is in the 2-position and is oxo; or $R^3$ is in the 3-position and is fluorine or amino wherein the amino group is optionally substituted by: hydroxy, $(C_{1-6})$alkylsulphonyl; trifluoromethylsulphonyl; $(C_{2-6})$alkenylsulphonyl; $(C_{1-6})$alkylcarbonyl; $(C_{2-6})$alkenylcarbonyl; $(C_{1-6})$alkoxycarbonyl; $(C_{2-6})$alkenyloxycarbonyl; $(C_{1-6})$alkyl; or $(C_{2-6})$alkenyl; wherein a $(C_{1-6})$alkyl or $(C_{2-6})$alkenyl moiety may be optionally substituted with up to 2 groups $R^{12}$ independently selected from:

halogen; $(C_{1-6})$alkylthio; trifluoromethyl; cyano; carboxy; tetrazolyl; 2-oxo-oxazolidinyl; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkylcarbonyl, $(C_{2-6})$alkenylcarbonyl or aminocarbonyl wherein the amino group is optionally substituted by $(C_{1-6})$alkyl, $(C_{2-6})$alkenyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl;

in addition when $R^3$ is disubstituted with a hydroxy or amino containing substituent and carboxy containing substituent these may together form a cyclic ester or amide linkage, respectively;

$R^4$ is a group —U—$R^5$ where
U is selected from CO, $SO_2$ and $CH_2$ and
$R^5$ is an optionally substituted bicyclic carbocyclic or heterocyclic ring system (A):

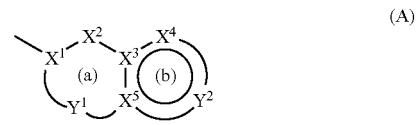

(A)

containing up to four heteroatoms in each ring in which
ring (a) is aromatic or non aromatic;
$X^1$ is C when part of an aromatic ring or $CR^{14}$ when part of a non aromatic ring;
$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
$X^4$ is N, $NR^{13}$, O, $S(O)_x$, CO or $CR^{14}$;
$X^3$ and $X^5$ are independently N or C;
$Y^1$ is a 1 to 3 atom linker group each atom of which is independently selected from N, $NR^{13}$, O, $S(O)_x$, CO and CR$^{14}$ when part of an aromatic or non-aromatic ring or may additionally be CR$^{14}$R$^{15}$ when part of a non aromatic ring, Y$^2$ is a 2 or 3 atom linker group completing an aromatic ring, each atom of Y$^2$ being independently selected from N, NR$^{13}$, O, S(O)$_x$, CO and CR$^{14}$;

each of R$^{14}$ and R$^{15}$ is independently selected from: H; (C$_{1-4}$)alkylthio; halo; carboxy(C$_{1-4}$)alkyl; halo(C$_{1-4}$)alkoxy; halo(C$_{1-4}$)alkyl; (C$_{1-4}$)alkyl; (C$_{2-4}$)alkenyl; (C$_{1-4}$)alkoxycarbonyl; formyl; (C$_{1-4}$)alkylcarbonyl; (C$_{2-4}$)alkenyloxycarbonyl; (C$_{2-4}$)alkenylcarbonyl; (C$_{1-4}$)alkylcarbonyloxy; (C$_{1-4}$)alkoxycarbonyl(C$_{1-4}$)alkyl; hydroxy; hydroxy(C$_{1-4}$)alkyl; mercapto(C$_{1-4}$)alkyl; (C$_{1-4}$)alkoxy; nitro; cyano; carboxy, amino or aminocarbonyl optionally substituted as for corresponding substituents in R$^3$; (C$_{1-4}$)alkylsulphonyl; (C$_{2-4}$)alkenylsulphonyl; or aminosulphonyl wherein the amino group is optionally mono- or di-substituted by (C$_{1-4}$)alkyl or (C$_{2-4}$)alkenyl; aryl; aryl(C$_{1-4}$)alkyl; aryl(C$_{1-4}$)alkoxy or R$^{14}$ and R$^{15}$ may together represent oxo;

each R$^{13}$ is independently H; trifluoromethyl; (C$_{1-4}$)alkyl optionally substituted by hydroxy, (C$_{1-6}$)alkoxy, (C$_{1-6}$)alkylthio, carboxy, halo or trifluoromethyl; (C$_{2-4}$)alkenyl; aryl; aryl (C$_{1-4}$)alkyl; arylcarbonyl; heteroarylcarbonyl; (C$_{1-4}$)alkoxycarbonyl; (C$_{1-4}$)alkylcarbonyl; formyl; (C$_{1-6}$)alkylsulphonyl; or aminocarbonyl wherein the amino group is optionally substituted by (C$_{1-4}$)alkoxycarbonyl, (C$_{1-4}$)alkylcarbonyl, (C$_{2-4}$)alkenyloxycarbonyl, (C$_{2-4}$)alkenylcarbonyl, (C$_{1-4}$)alkyl or (C$_{2-4}$)alkenyl and optionally further substituted by (C$_{1-4}$)alkyl or (C$_{2-4}$)alkenyl;

n is 0 or 1;

each x is independently 0, 1 or 2

A is NR$^{11}$, O or CR$^6$R$^7$ and B is NR$^{11}$, O, SO$_2$ or CR$^8$R$^9$ and wherein:

each of R$^6$, R$^7$, R$^8$ and R$^9$ is independently selected from: hydrogen; (C$_{1-6}$)alkoxy; (C$_{1-6}$)alkylthio; halo; trifluoromethyl; azido; (C$_{1-6}$)alkyl; (C$_{2-6}$)alkenyl; (C$_{1-6}$)alkoxycarbonyl; (C$_{1-6}$)alkylcarbonyl; (C$_{2-6}$)alkenyloxycarbonyl; (C$_{2-6}$)alkenylcarbonyl; hydroxy, amino or aminocarbonyl optionally substituted as for corresponding substituents in R$^3$; (C$_{1-6}$)alkylsulphonyl; (C$_{2-6}$)alkenylsulphonyl; or aminosulphonyl wherein the amino group is optionally substituted by (C$_{1-6}$)alkyl or (C$_{2-6}$)alkenyl;

or when n=R$^6$ and R$^8$ together represent a bond and R$^7$ and R$^9$ are as above defined;

or R$^6$ and R$^7$ or R$^8$ and R$^9$ together represent oxo;

provided that:

when A is NR$^{11}$, B is not NR$^{11}$ or O;

when A is CO, B is not CO, O or SO$_2$;

when n is 0 and A is NR$^{11}$, CR$^8$R$^9$ can only be CO;

when A is CR$^6$R$^7$ and B is SO$_2$, n is 0;

when n is 0, B is not NR$^{11}$ or O or R$^8$ and R$^9$ are not optionally substituted hydroxy or amino;

when A is O, B is not NR$^{11}$, O, SO$_2$ or CO and n=1; and when A-B is CR$^7$=CR$^9$, n is 1

R$^{10}$ is selected from (C$_{1-4}$)alkyl; (C$_{2-4}$)alkenyl and aryl any of which may be optionally substituted by a group R$^{12}$ as defined above; carboxy; aminocarbonyl wherein the amino group is optionally substituted by hydroxy, (C$_{1-6}$)alkyl, (C$_{2-6}$)alkenyl, (C$_{1-6}$)alkylsulphonyl, trifluoromethylsulphonyl, (C$_{2-6}$)alkenylsulphonyl, (C$_{1-6}$)alkoxycarbonyl, (C$_{1-6}$)alkylcarbonyl, (C$_{2-6}$)alkenyloxycarbonyl or (C$_{2-6}$)alkenylcarbonyl and optionally further substituted by (C$_{1-6}$)alkyl or (C$_{2-6}$)alkenyl; (C$_{1-6}$)alkylsulphonyl; trifluoromethylsulphonyl; (C$_{2-6}$)alkenylsulphonyl; (C$_{1-6}$)alkoxycarbonyl; (C$_{1-6}$)alkylcarbonyl; (C$_{2-6}$)alkenyloxycarbonyl; and (C$_{2-6}$)alkenylcarbonyl; and R$^{11}$ is hydrogen; trifluoromethyl, (C$_{1-6}$)alkyl; (C$_{2-6}$)alkenyl; (C$_{1-6}$)alkoxycarbonyl; (C$_{1-6}$)alkylcarbonyl; or aminocarbonyl wherein the amino group is optionally substituted by (C$_{1-6}$)alkoxycarbonyl, (C$_{1-6}$)alkylcarbonyl, (C$_{2-6}$)alkenyloxycarbonyl, (C$_{2-6}$)alkenylcarbonyl, (C$_{1-6}$)alkyl or (C$_{2-6}$)alkenyl and optionally further substituted by (C$_{1-6}$)alkyl or (C$_{2-6}$)alkenyl;

or where one of R$^3$ and R$^6$, R$^7$, R$^8$ or R$^9$ contains a carboxy group and the other contains a hydroxy or amino group they may together form a cyclic ester or amide linkage.

This invention also provides a method of treatment of bacterial infections in mammals, particularly in man, which method comprises the administration to a mammal in need of such treatment an effective amount of a compound of formula (I), or a pharmaceutically acceptable derivative thereof.

The invention also provides the use of a compound of formula (I), or a pharmaceutically acceptable derivative thereof, in the manufacture of a medicament for use in the treatment of bacterial infections in mammals.

The invention also provides a pharmaceutical composition comprising a compound of formula (I), or a pharmaceutically acceptable derivative thereof, and a pharmaceutically acceptable carrier.

Preferably one of Z$^1$, Z$^2$, Z$^3$, Z$^4$ and Z$^5$ is N, one is CR$^{1a}$ and the remainder are CH, or one of Z$^1$, Z$^2$, Z$^3$, Z$^4$ and Z$^5$ is CR$^{1a}$ and the remainder are CH.

Preferably Z$^5$ is CH, C—Cl or N, Z$^3$ is CH or CF and Z$^1$, Z$^2$ and Z$^4$ are each CH, or Z$^1$ is N, Z$^3$ is CH and Z$^2$ and Z$^4$ are each CH and Z$^5$ is CH or C—Cl.

When R$^1$ or R$^{1a}$ is substituted alkoxy it is preferably (C$_{2-6}$)alkoxy substituted by optionally N-substituted amino, guanidino or amidino, or (C$_{1-6}$)alkoxy substituted by piperidyl. Suitable examples of R$^1$ and R$^{1a}$ alkoxy include methoxy, trifluoromethoxy, n-propyloxy, iso-butyloxy, aminoethyloxy, aminopropyloxy, aminobutyloxy, aminopentyloxy, guanidinopropyloxy, piperidin-4-ylmethyloxy, phthalimido pentyloxy or 2-aminocarbonylprop-2-oxy.

Preferably R$^1$ and R$^{1a}$ are independently methoxy, (C$_{1-6}$)alkyl, (C$_{1-6}$)alkylthio, amino(C$_{3-5}$)alkyloxy, guanidino(C$_{3-5}$)alkyloxy, piperidyl(C$_{3-5}$)alkyloxy, nitro, fluoro or chloro; R$^1$ is more preferably methoxy, fluoro or chloro. R$^{1a}$ is more preferably H, F or Cl. Most preferably R$^1$ is methoxy. and R$^{1a}$ is H or when Z$^3$ is CR$^{1a}$ it may be C—F or when Z$^5$ is CR$^{1a}$ it maybe C—F or C—Cl.

When Z$^5$ is CR$^{1a}$, R$^{1a}$ is preferably hydrogen, chloro, cyano, hydroxymethyl or carboxy, most preferably hydrogen or chloro.

Preferably n is 0.

R$^2$ is preferably hydrogen; (C$_{1-4}$)allyl substituted with carboxy, optionally substituted hydroxy, optionally substituted aminocarbonyl, optionally substituted amino or (C$_{1-4}$)alkoxycarbonyl; or (C$_{2-4}$)alkenyl substituted with (C$_{1-4}$)alkoxycarbonyl or carboxy. More preferred groups for R$^2$ are hydrogen, carboxymethyl, hydroxyethyl, aminocarbonylmethyl, ethoxycarbonylmethyl, ethoxycarbonylallyl and carboxyallyl, most preferably hydrogen.

Examples of R$^3$ include CF$_3$, fluoro and oxo.

When R$^3$ is amino it is preferably unsubstituted or substituted by (C$_{1-6}$)alkyl or (C$_{2-6}$)alkenyl.

R$^3$ is preferably in the 3- or 4-position.

Most preferably R$^3$ is 3-F and more preferably it is cis to (NR$^2$)R$^4$.

Preferably n=0.

When A is CH(OH) the R-stereochemistry is preferred.

Preferably A is NH, NCH$_3$, CH$_2$, CHOH, CH(NH$_2$), C(Me)(OH) or CH(Me).

Preferably B is CH$_2$ or CO.

Preferably A-B is CHOH—CH$_2$, NR$^{11}$—CH$_2$, NR$^{11}$—CO or CH$_2$—CH$_2$.

Particularly preferred are those compounds where n=0, A is NH and B is CO, or A is CH$_2$ or CHOH and B is CH$_2$, when more preferably A is the R-isomer of CHOH.

Preferably R$^{11}$ is hydrogen or (C$_{1-4}$)alkyl e.g. methyl, more preferably hydrogen.

U is most preferably CH$_2$.

Preferably R$^5$ is an aromatic heterocyclic ring (A) having 1–4 heteroatoms of which one is N or NR$^{13}$, more preferably an aromatic heterocyclic ring (A) having 8–11 ring atoms including 2–4 heteroatoms of which at least one is N or NR$^{13}$ in which preferably Y$^2$ contains 2–3 heteroatoms, one of which is S and 1–2 are N, with one N bonded to X$^3$.

Examples of Rings (A) Include Optionally Substituted:

(a) and (b) Aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2yl, benzimidazol-2-yl, benzothiophen-2-yl, 1H-benzothiazol-5-yl, 1H-indol-5-yl, 3H-benzoxazol-2-one-6-yl, 3H-benzooxazol-2-thione-6-yl, 3H-benzothiazol-2-one-5-yl, 3H-quinazolin-4-one-2-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimidin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thiazolo[5,4-b]pyridin-6-yl, thieno[3,2-b]pyridin-6-yl, 4-oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl, 2H-isoquinolin-1-one-3-yl.

(a) is Non Aromatic (2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-(2,3-dihydro-[1,4]dioxino[2,3-b]pyridin-3-yl, 2,3-dihydro-[1,4]dioxino[2,3-b]pyridin-3-yl, 3-substituted-3H-quinazolin-4-one-2-yl, 2,3-dihydro-benzo[1,4]dioxan-2-yl, 1-oxo-1,3,4,5-tetrahydrobenzo[c]azepin-2-yl.

In one aspect, when R$^{13}$ is optionally substituted (C$_{1-4}$)alkyl, the optional substituent is other than carboxy.

R$^{13}$ is preferably H if in ring (a) or in addition (C$_{1-4}$)alkyl such as methyl or isopropyl when in ring (b). More preferably, in ring (b) R$^{13}$ is hydrogen when NR$^{13}$ is bonded to X$^3$ and (C$_{1-4}$)alkyl when NR$^{13}$ is bonded to X$^5$.

R$^{14}$ and R$^{15}$ are preferably independently selected from hydrogen, halo, hydroxy, (C$_{1-4}$)alkyl, (C$_{1-4}$)alkoxy, trifluoromethoxy, nitro, cyano, aryl(C$_{1-4}$)alkoxy and (C$_{1-4}$)alkylsuphonyl. More preferably R$^{15}$ is hydrogen.

More preferably each R$^{14}$ is selected from hydrogen, chloro, fluoro, hydroxy, methyl, methoxy, trifluoromethoxy, benzyloxy, nitro, cyano and methylsulphonyl. Most preferably R$^{14}$ is selected from hydrogen, hydroxy, fluorine or nitro. Preferably 0–3 groups R$^{14}$ are substituents other than hydrogen. Preferably when R$^{14}$ is not hydrogen, X$^4$ is CR$^{14}$ and/or CR$^{14}$ is a component of Y$^2$.

Most preferred groups R$^5$ include 4,6-difluoro-indol-2-yl, 1H-pyrrolo[2,3-b]-pyridin-2-yl, 1H-pyrrolo[3,2-b]-pyridin-2-yl, 8-hydroxy-quinolin-2-yl, quinoxalin-2-yl, benzimidazol-2-yl, benzo[1,2,3]-thiadiazol-5-yl, benzothiophen-2-yl, 4,6-difluoro-1H-benzimidazol-2-yl, benzothiazole-5-yl and 3-(R)-2,3-dihydro-[1,4]dioxino[2,3-b]pyridin-3-yl, [1,2,3]thiadiazolo[5,4-b]pyridin-6-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo. Haloalkyl moieties include 1–3 halogen atoms.

Unless otherwise defined, the term "heterocyclic" as used herein includes optionally substituted aromatic and non-aromatic, single and fused, rings suitably containing up to four hetero-atoms in each ring selected from oxygen, nitrogen and sulphur, which rings may be unsubstituted or C-substituted by, for example, up to three groups selected from (C$_{1-4}$)alkylthio; halo; carboxy(C$_{1-4}$)alkyl; halo(C$_{1-4}$)alkoxy; halo(C$_{1-4}$)alkyl; (C$_{1-4}$)alkyl; (C$_{2-4}$)alkenyl; (C$_{2-4}$)alkoxycarbonyl; formyl; (C$_{1-4}$)alkylcarbonyl; (C$_{2-4}$)alkenyloxycarbonyl; (C$_{2-4}$)alkenylcarbonyl; (C$_{1-4}$)alkylcarbonyloxy; (C$_{1-4}$)alkoxycarbonyl(C$_{1-4}$)alkyl; hydroxy; hydroxy(C$_{1-4}$)alkyl; mercapto(C$_{1-4}$)alkyl; (C$_{1-4}$)alkoxy; nitro; cyano, carboxy; amino or aminocarbonyl optionally substituted as for corresponding substituents in R$^3$; (C$_{1-4}$)alkylsulphonyl; (C$_{2-4}$)alkenylsuphonyl; or aminosulphonyl wherein the amino group is optionally substituted by (C$_{1-4}$)alkyl or (C$_{2-4}$)alkenyl; optionally substituted aryl, aryl(C$_{1-4}$)alkyl or aryl(C$_{1-4}$)alkoxy and oxo groups.

Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; (C$_{1-4}$)alkyl optionally substituted by hydroxy, (C$_{1-6}$)alkoxy, (C$_{1-6}$)alkylthio, halo or trifluoromethyl; (C$_{2-4}$)alkenyl; aryl; aryl (C$_{1-4}$)alkyl; (C$_{1-4}$)alkoxycarbonyl; (C$_{1-4}$)alkylcarbonyl; formyl; (C$_{1-6}$)alkylsulphonyl; or aminocarbonyl wherein the amino group is optionally substituted by (C$_{1-4}$)alkoxycarbonyl, (C$_{1-4}$)alkylcarbonyl, (C$_{2-4}$)alkenyloxycarbonyl, (C$_{2-4}$)alkenylcarbonyl, (C$_{1-4}$)alkyl or (C$_{2-4}$)alkenyl and optionally further substituted by (C$_{1-4}$)alkyl or (C$_{2-4}$)alkenyl.

When used herein the term "aryl", includes optionally substituted phenyl and naphthyl.

Aryl groups may be optionally substituted with up to five, preferably up to three, groups selected from (C$_{1-4}$)alkylthio; halo; carboxy(C$_{1-4}$)alkyl; halo(C$_{1-4}$)alkoxy; halo(C$_{1-4}$)alkyl; (C$_{1-4}$)alkyl; (C$_{2-4}$)alkenyl; (C$_{2-4}$)alkoxycarbonyl; formyl;

($C_{1-4}$)alkylcarbonyl; ($C_{2-4}$)alkenyloxycarbonyl; ($C_{2-4}$)alkenylcarbonyl; ($C_{1-4}$)alkylcarbonyloxy; ($C_{2-4}$)alkoxycarbonyl($C_{1-4}$)alkyl; hydroxy; hydroxy($C_{1-4}$)alkyl; mercapto ($C_{1-4}$)allyl; ($C_{1-4}$)alkoxy; nitro; cyano; carboxy; amino or aminocarbonyl optionally substituted as for corresponding substituents in $R^3$; ($C_{1-4}$)alkylsulphonyl; ($C_{2-4}$)alkenylsulphonyl; or aminosulphonyl wherein the amino group is optionally substituted by ($C_{1-4}$)allyl or ($C_{2-4}$)alkenyl; phenyl, phenyl($C_{1-4}$)alkyl or phenyl($C_{1-4}$)alkoxy The term "acyl" includes formyl and ($C_{1-6}$)alkylcarbonyl group.

Some of the compounds of this invention maybe crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Particular compounds according to the invention include those mentioned in the examples and their pharmaceutically acceptable derivatives.

Pharmaceutically acceptable derivatives of the abovementioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharnaceutically acceptable in vivo hydrolysable ester-forming groups include those forming esters which break down readily in the human body to leave the parent acid or its salt. Suitable groups of this type include those of part formulae (i), (ii), (iii), (iv) and (v):

(i)

$$-\overset{R^a}{\underset{|}{CH}}-O \cdot CO \cdot R^b$$

(ii)

$$-R^c-N\overset{R^d}{\underset{R^e}{\diagdown}}$$

(iii)

$$-CH_2-OR^f$$

(iv)

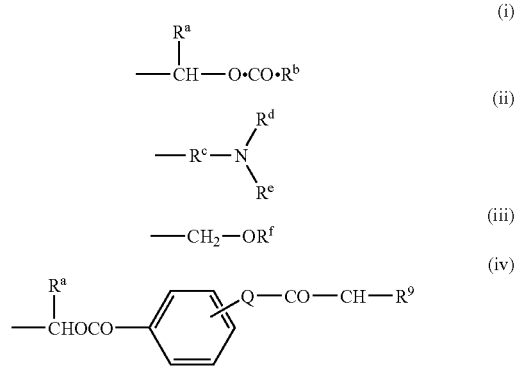

-continued

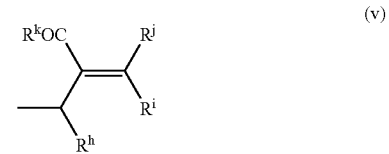

(v)

wherein $R^a$ is hydrogen, ($C_{1-6}$) alkyl, ($C_{3-7}$) cycloalkyl, methyl, or phenyl, $R^b$ is ($C_{1-6}$) alkyl, ($C_{1-6}$) alkoxy, phenyl, benzyl, ($C_{3-7}$) cycloalllyl, ($C_{3-7}$) cycloalkyloxy, ($C_{1-6}$) alkyl ($C_{3-7}$) cycloalkyl, 1-amino ($C_{1-6}$) alkyl, or 1-($C_{1-6}$ alkyl) amino ($C_{1-6}$) alkyl; or $R^a$ and $R^b$ together form a 1,2-phenylene group optionally substituted by one or two methoxy groups; $R^c$ represents ($C_{1-6}$) alkylene optionally substituted with a methyl or ethyl group and $R^d$ and $R^e$ independently represent ($C_{1-6}$) alkyl; $R^f$ represents ($C_{1-6}$) alkyl; $R^g$ represents hydrogen or phenyl optionally substituted by up to three groups selected from halogen, ($C_{1-6}$) alkyl, or ($C_{1-6}$) alkoxy; Q is oxygen or NH; $R^h$ is hydrogen or ($C_{1-6}$) alkyl; $R^i$ is hydrogen, ($C_{1-6}$) alkyl optionally substituted by halogen, ($C_{2-6}$) alkenyl, ($C_{1-6}$) alkoxycarbonyl, aryl or heteroaryl; or $R^h$ and $R^i$ together form ($C_{1-6}$) alklene; $R^j$ represents hydrogen, ($C_{1-6}$) alkyl or ($C_{1-6}$) alkoxycarbonyl; and $R^k$ represents ($C_{1-8}$) alkyl, ($C_{1-8}$) alkoxy, ($C_{1-6}$) alkoxy($C_{1-6}$)alkoxy or aryl.

Examples of suitable in vivo hydrolysable ester groups include, for example, acyloxy($C_{1-6}$)alkyl groups such as acetoxyrnethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; ($C_{1-6}$)alkoxycarbonyloxy($C_{1-6}$)alkyl groups, such as ethoxycarbonyloxymethyl, α-ethoxycarbonyloxyethyl and propoxycarbonyloxyethyl; di($C_{1-6}$)alkYlamino($C_{1-6}$)alkyl especially di($C_{1-4}$)alkylamino($C_{1-4}$)alkyl groups such as dimethylaminomethyl, dimethylarinoethyl, diethylaminomethyl or diethylaminoethyl; 2-(($C_{1-6}$)alkoxycarbonyl)-2-($C_{2-6}$)alkenyl groups such as 2-(isobutoxycarbonyl)pent-2-enyl and 2-(ethoxycarbonyl)but-2-enyl; lactone groups such as phthalidyl and dimethoxyphthalidyl.

A furter suitable pharmaceutically acceptable in vivo hydrolysable ester-forming group is that of the formula:

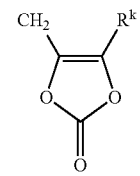

wherein $R^k$ is hydrogen, $C_{1-6}$ alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes compound in which an A-B group CH(OH)—$CH_2$ is in either isomeric configuration, the R-isomer is preferred. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), and pharmaceutically acceptable derivatives thereof, which process comprises:

reacting a compound of formula (IV) with a compound of formula (V):

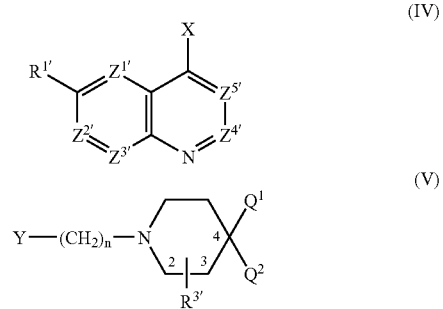

wherein n is as defined in formula (I); $Z^{1\prime}$, $Z^{2\prime}$, $Z^{3\prime}$, $Z^{4\prime}$, $Z^{5\prime}$, $R^{1\prime}$ and $R^{3\prime}$ are $Z^1$, $Z^2$, $Z^3$, $Z^4$, $Z^5$, $R^1$ and $R^3$ as defined in formula (I) or groups convertible thereto;

$Q^1$ is $NR^{2\prime}R^{4\prime}$ or a group convertible thereto wherein $R^{2\prime}$ and $R^{4\prime}$ are $R^2$ and $R^4$ as defined in formula (I) or groups convertible thereto and $Q^2$ is H or $R^{3\prime}$ or $Q^1$ and $Q^2$ together form an optionally protected oxo group;

and X and Y may be the following combinations:
(i) X is A'-COW, Y is H and n is 0;
(ii) X is $CR^6$=$CR^8R^9$, Y is H and n is 0;
(iii) X is oxirane, Y is H and n is 0;
(iv) X is N=C=O and Y is H and n is 0;
(v) one of X and Y is $CO_2R^y$ and the other is $CH_2CO_2R^x$;
(vi) X is $CHR^6R^7$ and Y is C(=O)$R^9$;
(vii) X is $CR^7$=$PR^z_3$ and Y is C(=O)$R^9$ and n=1;
(viii) X is C(=O)$R^7$ and Y is $CR^9$=$PR^z_3$ and n=1;
(ix) Y is COW and X is $NHR^{11\prime}$ or $NR^{11\prime}$COW and n=0 or 1 or when n=1 X is COW and Y is $NHR^{11\prime}$ or $NR^{11\prime}$COW;
(x) X is C(O=)$R^6$ and Y is $NHR^{11\prime}$ or X is $NHR^{11\prime}$ and Y is C(=O)$R^8$ and n=1;
(xi) X is $NHR^{11\prime}$ and Y is $CR^8R^9W$ and n=1;
(xii) X is $CR^6R^7W$ and Y is $NHR^{11\prime}$ or OH and n=1;
(xiii) X is $CR^6R^7SO_2W$ and Y is H and n=0;
(xiv) X is W or OH and Y is $CH_2OH$ and n=1;
(xv) X is $NHR^{11\prime}$ and Y is $SO_2W$ or X is $NR^{11\prime}SO_2W$ and Y is H, and n=0;
(xvi) X is $NR^{11\prime}COCH_2W$ or $NR^{11\prime}SO_2CH_2W$ and Y is H and n=0;
(xvii) X is W and Y is $CONHR^{11\prime}$;

in which W is a leaving group, e.g. halo or imidazolyl; $R^x$ and $R^y$ are $(C_{1-6})$alkcyl; $R^z$ is aryl or $(C_{1-6})$alkyl; A' and $NR^{11\prime}$ are A and $NR^{11}$ as defined in formula (I), or groups convertible thereto; and oxirane is:

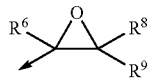

wherein $R^6$, $R^8$ and $R^9$ are as defined in formula (I);
and thereafter optionally or as necessary converting $Q^1$ and $Q^2$ to $NR^{2\prime}R^{4\prime}$; converting A', $Z^{1\prime}$, $Z^{2\prime}$, $Z^{3\prime}$, $Z^{4\prime}$, $Z^{5\prime}$, $R^{1\prime}$, $R^{2\prime}$, $R^{3\prime}$, $R^{4\prime}$ and $NR^{11\prime}$ to A, $Z^1$, $Z^2$, $Z^3$, $Z^4$, $Z^5$, $R^1$, $R^2$, $R^3$, $R^4$ and $NR^{11}$; converting A-B to other A-B, interconverting $R^1$, $R^2$, $R^3$ and/or $R^4$, and/or forming a pharmaceutically acceptable derivative thereof.

Process variant (i) initially produces compounds of formula (I) wherein A-B is A'-CO.

Process variant (ii) initially produces compounds of formula (I) wherein A-B is $CHR^6$—$CR^8R^9$.

Process variant (iii) initially produces compounds of formula (I) wherein A-B is $CR^6(OH)$—$CR^8R^9$.

Process variant (iv) initially produces compounds of formula (I) where A-B is NH—CO.

Process variant (v) initially produces compounds of formula (I) wherein A-B is CO—$CH_2$ or $CH_2$—CO.

Process variant (vi) initially produces compounds of formula (I) wherein A-B is $CR^6R^7$—$CR^9OH$.

Process variant (vii) and (viii) initially produce compounds of formula (I) wherein A-B is $CR^7$=$CR^9$.

Process variant (ix) initially produces compounds of formula (I) where A-B is CO—$NR^{11}$ or $NR^{11}$—CO.

Process variant (x) initially produces compounds of formula (I) wherein A-B is $CHR^6$—$NR^{11}$ or $NR^{11}$—$CHR^8$.

Process variant (xi) initially produces compounds of formula (I) wherein A-B is $NR^{11\prime}$—$CR^8R^9$.

Process variant (xii) initially produces compounds of formula (I) wherein A-B is $CR^6R^7$—$NR^{11\prime}$ or $CR^6R^7$—O.

Process variant (xiii) initially produces compounds of formula (I) where A-B is $CR^6R^7$—$SO_2$.

Process variant (xiv) initially produces compounds of formula (I) wherein A-B is O—$CH_2$.

Process variant (xv) initially produces compounds where AB is $NR^{11}SO_2$.

Process variant (xvi) initially produces compounds of formula (I) where A-B is $NR^{11\prime}$—CO or $NR^{11\prime}$—$SO_2$ and n=1.

Process variant (xvii) initially produces compounds of formula (I) where A-B is $NR^{11\prime}$—CO.

In process variants (i) and (ix) the reaction is a standard amide or urea formation reaction involving e.g.:

1. Activation of a carboxylic acid (e.g. to an acid chloride, mixed anhydride, active ester, O-acyl-isourea or other species), and treatment with an amine (Ogliaruso, M. A.; Wolfe, J. F. in *The Chemistry of Functional Groups* (Ed. Patai, S.) Suppl. B: *The Chemistry of Acid Derivatives*, Pt. 1 (John Wiley and Sons, 1979), pp 442–8; Beckwith, A. L. J. in *The Chemistry of Functional Groups* (Ed. Patai, S.) Suppl. B: *The Chemistry of Amides* (Ed. Zabricky, J.) (John Wiley and Sons, 1970), p73 ff. The acid and amide are preferably reacted in the presence of an activating agent such as 1-(dimethylaminopropyl)-3-ethylcarbodi-imide hydrochloride (EDC) or 1-hydroxybenzotriazole (HOBT) or O-(7-azabenzotriazol-1-yl)-N,N,N',N'-tetramethyluronium hexafluorophosphate (HATU); or 2. The specific methods of:
a. in situ conversion of an acid into the amine component by a modified Curtius reaction procedure (Shioiri, T., Murata, M., Hamada, Y., *Chem. Pharm. Bull.* 1987, 35, 2698)
b. in situ conversion of the acid component into the acid chloride under neutral conditions (Villeneuve, G. B.; Chan, T. H., *Tetrahedron. Lett.* 1997, 38, 6489).

A' may be, for example protected hydroxymethylene.

The process variant (ii) is a standard addition reaction using methods well known to those skilled in the art. The process is preferably carried out in a polar organic solvent e.g. racetonitrile in the presence of an organic base e.g. triethylamine.

In process variant (iii) the coupling may be effected in acetonitrile at room temperature in the presence of one equivalent of lithium perchlorate as catalyst (general method of J. E. Chateauneuf et al, *J. Org. Clem.*, 56, 5939–5942, 1991) or more preferably with ytterbium triflate in dichloromethane. In some cases an elevated temperature such as 40–70° C. may be beneficial. Alternatively, the piperidine may be treated with a base, such as one equivalent of butyl lithium, and the resulting salt reacted with the oxirane in an inert solvent such as tetrahydrofiran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

The process variant (iv) is a standard urea formation reaction from the reaction of an isocyanate with an amine and is conducted by methods well known to those skilled in the art (for example see March, J; *Advanced Organic Chemistry, Edition* 3 (John Wiley and Sons, 1985), p802–3). The process is preferably carried out in a polar solvent such as N,N-dimethylformamide.

In process variant (v) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0–100° C. Analogous routes are described in DE330945, EP31753, EP53964 and H. Sargent, J. Am. Chem. Soc. 68, 2688–2692 (1946). Similar Claisen methodology is described in Soszko et. al., Pr.Kom.Mat. Przyr.Poznan.Tow.Przj.Nauk., (1962), 10, 15.

In process variant (vi) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. (analogous process in Gutswiller et al. (1978) J. Am. Chem. Soc. 100, 576).

In process variants (vii) and (viii) if a base is used it is preferably NaH, KH, an alkyl lithium e.g. Buli, a metal alkoxide e.g. NaOEt, sodamide or lithium dialkylamide e.g. di-isopropylamide. An analogous method is described in U.S. Pat. No. 3,989,691 and M. Gates et. al. (1970) J. Amer. Chem. Soc., 92, 205, as well as Taylor et al. (1972) JACS 94, 6218.

In process variant (x) where X or Y is CHO the reaction is a standard reductive alkylation using, e.g., sodium borohydride or sodium triacetoxyborohydride (Gribble, G. W. in *Encyclopedia of Reagents for Organic Synthesis (Ed. Paquette, L. A)* (John Wiley and Sons, 1995), p 4649).

The process variants (xi) and (xii) are standard alkylation reactions well known to those skilled in the art, for example where an alcohol or amine is treated with an alkyl halide in the presence of a base (for example see March, J; *Advanced Organic Chemistry, Edition* 3 (John Wiley and Sons, 1985), p364–366 and p342–343). The process is preferably carried out in a polar solvent such as N,N-dimethylformamide In process variant (xiii) the reaction is a standard sulphonamide formation reaction well known to those skilled in the art. This may be e.g. the reaction of a sulphonyl halide with an amine.

In process variant (xiv) where X is W such as halogen, methanesulphonyloxy or trifluoromethanesulphonyloxy, the hydroxy group in Y is preferably converted to an OM group where M is an alkali metal by treatment of an alcohol with a base. The base is preferably inorganic such as NaH, lithium diisopropylamide or sodium. Where X is OH, the hydroxy group in Y is activated under Mitsunobu conditions (Fletcher et.al. J Chem Soc. (1995), 623). Alternatively the X=O and Y=CH$_2$OH groups can be reacted directly by activation with dichlorocarbodiimide (DCC) (Chem. Berichte 1962, 95, 2997 or Angewante Chemie 1963 75, 377).

In process variant (xv) the reaction is conducted in the presence of an organic base such as triethylamine or pyridine such as described by Fuhrman et.al., J. Amer. Chem. Soc.; 67, 1245, 1945. The X=NR$^{11}$'SO$_2$W or Y=SO$_2$W intermediates can be formed from the requisite amine e.g. by reaction with SO$_2$Cl$_2$ analogously to the procedure described by the same authors Fuhrman et.al., J. Amer. Chem. Soc.; 67, 1245, 1945.

In process variant (xvi) the reaction is an alkylation, examples of which are described in J. Med. chem. (1979) 22(10) 1171–6. The compound of formula (IV) may be prepared from the corresponding compound where X is NHR$^{11}$' by acylation with an appropriate derivative of the acid WCH$_2$COOH such as the acid chloride or sulphonation with an appropriate derivative of the sulphonic acid WCH$_2$SO$_3$H such as the sulphonyl chloride.

In process variant (xvii) the leaving group W is preferably chloro or trifluoromethylsulphonyl and the reaction is the palladium catalysed process known as the "Buchwald" reaction (J. Yin and S. L. Buchwald, Org. Lett., 2000, 2, 1101).

Reduction of a carbonyl group A or B to CHOH can be readily accomplished using reducing agents well known to those skilled in the art, e.g. sodium borohydride in aqueous ethanol or lithium aluminium hydride in ethereal solution. This is analogous to methods described in EP53964, U.S. Pat. No. 384,556 and J. Gutzwiller et al, *J. Amer. Chem. Soc.*, 1978, 100, 576.

The carbonyl group A or B may be reduced to CH$_2$ by treatment with a reducing agent such as hydrazine in ethylene glycol, at e.g. 130–160° C., in the presence of potassium hydroxide.

Reaction of a carbonyl group A or B with an organometallic reagent yields a group where R$^8$ is OH and R$^9$ is alkyl.

A hydroxy group on A or B may be oxidised to a carbonyl group by oxidants well known to those skilled in the art, for example, manganese dioxide, pyridinium chlorochromate or pyridinium dichromate.

A hydroxyalkyl A-B group CHR$^7$CR$^9$OH or CR$^7$(OH)CHR$^9$ may be dehydrated to give the group CR$^7$=CR$^9$ by treatment with an acid anhydride such as acetic anhydride.

Methods for conversion of CR$^7$=CR$^9$ by reduction to CHR$^7$CHR$^9$ are well known to those skilled in the art, for example using hydrogenation over palladium on carbon as catalyst. Methods for conversion of CR$^7$=CR$^9$ to give the A-B group CR$^7$(OH)CHR$^9$ or CHR$^7$CR$^9$OH are well known to those skilled in the art for example by epoxidation and subsequent reduction by metal hydrides, hydration, hydroboration or oxymercuration.

An amide carbonyl group may be reduced to the corresponding amine using a reducing agent such as lithium aluminium hydride.

A hydroxy group in A or B may be converted to azido by activation and displacement e.g. under Mitsunobu conditions using hydrazoic acid or by treatment with diphenylphosphorylazide and base, and the azido group in turn may be reduced to amino by hydrogenation.

An example of a group $Q^1$ convertible to $NR^2 R^4$ is $NR^{2'}R^{4'}$ or halogen. Halogen may be displaced by an amine $HNR^{2'}R^{4'}$ by a conventional alkylation.

When $Q^1$ $Q^2$ together form a protected oxo group this maybe an acetal such as ethylenedioxy which can subsequently be removed by acid treatment to give a compound of formula (VI):

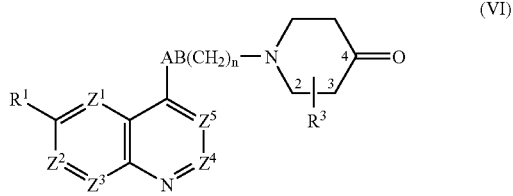

(VI)

wherein the variables are as described for formula (I)

Intermediates of formula (VI) are novel and as such form part of the invention.

The ketone of formula (VI) is reacted with an amine $HNR^{2'}R^{4'}$ by conventional reductive alkylation as described above for process variant (x).

Examples of groups $Z^{1'}, Z^{2'}, Z^{3'}, Z^{4'}, Z^{5'}$ convertible to $Z^1$, $Z^2$, $Z^3$, $Z^4$ and $Z^5$ include $CR^{1a'}$ where $R^{1a'}$ is a group convertible to $R^{1a}$. $Z^{1'}, Z^{2'}, Z^{3'}, Z^{4'}$ and $Z^{5'}$ are preferably $Z^1$, $Z^2$, $Z^3$, $Z^4$ and $Z^5$.

$R^{1a'}, R^{1'}$ and $R^{2'}$ are preferably $R^{1a}, R^1$ and $R^2$. $R^{1'}$ is preferably methoxy. $R^{2'}$ is preferably hydrogen. $R^{3'}$ is $R^3$ or more preferably hydrogen, vinyl, alkoxycarbonyl or carboxy. $R^{4'}$ is $R^4$ or more preferably H or an N-protecting group such as t-butoxycarbonyl, benzyloxycarbonyl or 9-fluorenylmethyloxycarbonyl.

Conversions of $R^{1'}, R^{2'}, R^{3'}$ and $R^{4'}$ and interconversions of $R^1, R^2, R^3$ and $R^4$ are conventional. In compounds which contain an optionally protected hydroxy group, suitable conventional hydroxy protecting groups which may be removed without disrupting the remainder of the molecule include acyl and alkylsilyl groups. N-protecting groups are removed by conventional methods.

For example $R^{1'}$ methoxy is convertible to $R^{1'}$ hydroxy by treatment with lithium and diphenylphosphine (general method described in Ireland et al, J. Amer. Chem. Soc., 1973, 7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

Substituted 2-oxo-oxazolidinyl containing $R^3$ groups may be prepared from the corresponding aldehyde by conventional reaction with a glycine anion equivalent, followed by cyclisation of the resulting amino alcohol (M. Grauert et al, Ann. Chem., 1985, 1817; Rozenberg et al, Angew. Chem. Int. Ed. Engl., 1994, 33(1), 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols $CH_2OH$ using chromium acid and sulphuric acid in water/methanol (E. R. H. Jones et al, J. Chem. Soc., 1946, 39). Other oxidising agents may be used for this transformation such as sodium periodate catalysed by ruthenium trichloride (G. F. Tutwiler et al, J. Med. Chem., 1987, 30(6) 1094), chromium trioxide-pyridine (G. Just et al, Synth. Commun., 1979, 9(7), 613), potassium permanganate (D. E. Reedich et al, J. Org. Chem.,1985, 50(19), 3535), and pyridinium chlorochromate (D. Askin et al, Tetrahedron Lett., 1988, 29(3) 277).

The carboxy group may alternatively be formed in a two stage process, with an initial oxidation of the alcohol to the corresponding aldehyde using for instance dimethyl sulphoxide activated with oxalyl chloride (N. Cohen et al, J. Am. Chem. Soc., 1983, 105, 3661) or dicyclohexylcarbodiimide (R. M. Wengler, Angew. Chim. Int. Ed. Eng., 1985, 24(2), 77), or oxidation with tetrapropylammonium perruthenate (Ley et al, J. Chem. Soc. Chem Commun.,1987, 1625). The aldehyde may then be separately oxidised to the corresponding acid using oxidising agents such as silver (II) oxide (R. Grigg et al, J. Chem. Soc. Perlin 1,1983, 1929), potassium permanganate (A. Zurcher, Helv. Chim. Acta., 1987, 70 (7), 1937), sodium periodate catalysed by ruthenium trichloride (T. Sakata et al, Bull. Chem. Soc. Jpn., 1988, 61(6), 2025), pyridinium chlorochromate (R. S. Reddy et al, Synth. Commun., 1988, 18(51), 545) or chromium trioxide (R. M. Coates et al, J. Am. Chem. Soc.,1982, 104, 2198).

An $R^3$ $CO_2H$ group may also be prepared from oxidative cleavage of the corresponding diol, $CH(OH)CH_2OH$, using sodium periodate catalysed by ruthenium trichloride with an acetontrile-carbontetrachloride-water solvent system (V. S. Martin et al, Tetrahedron Letters, 1988, 29(22), 2701).

Other routes to the synthesis of carboxy groups within $R^3$ are well known to those skilled in the art.

$R^3$ groups containing a cyano or carboxy group may be prepared by conversion of an alcohol to a suitable leaving group such as the corresponding tosylate by reaction with para-toluenesulphonyl chloride (M. R. Bell, J. Med. Chem., 1970, 1, 389), or the iodide using triphenylphosphine, iodine, and imidazole (G. Lange, Synth. Commun., 1990, 20, 1473). The second stage is the displacement of the leaving group with cyanide anion (L. A. Paquette et al, J. Org. Chem.,1979, 44(25), 4603; P. A. Grieco et al, J. Org. Chem., 1988, 53(16), 3658. Finally acidic hydrolysis of the nitrile group gives the desired acids (H. Rosemeyer et al, Heterocycles, 1985, 23 (10), 2669). The hydrolysis may also be carried out with base e.g. potassium hydroxide (H. Rapoport, J. Org. Chem., 1958, 23, 248) or enzymatically (T. Beard et al, Tetrahedron Asymmetry, 1993, 4 (6), 1085).

$R^{3'}$ cis or trans hydroxy may be introduced by the methods of van Deale et al., Drug Development Research 8:225–232 (1986) or Heterocycles 39(1), 163–170 (1994). For trans hydroxy, a suitable method converts N-protected tetrahydropyridine to the epoxide by treatment with metachloroperbenzoic acid, followed by opening of the epoxide with a suitable amine $NR^{2'}R^{4'}$. $R^{3'}$ hydroxy may then be converted to optionally substituted amino via preparation of the $R^{3'}$ amino derivative by standard transformations such as a Mitsunobu reaction (for example as reviewed in Misunobu, Synthesisi, (1981), 1), for example with succinimide in the presence of diethylazodicarboxylate and triphenylphosphine to give the phthalimidoethylpiperidine. Removal of the phthaloyl group, for example by treatment with methylhydrazine, affords the $R^{3'}$ amine. Optional substitution may then be introduced by standard methods for amine substitution well known to those skilled in the art.

$R^3$ 4-$CF_3$ may be introduced by the following scheme I:

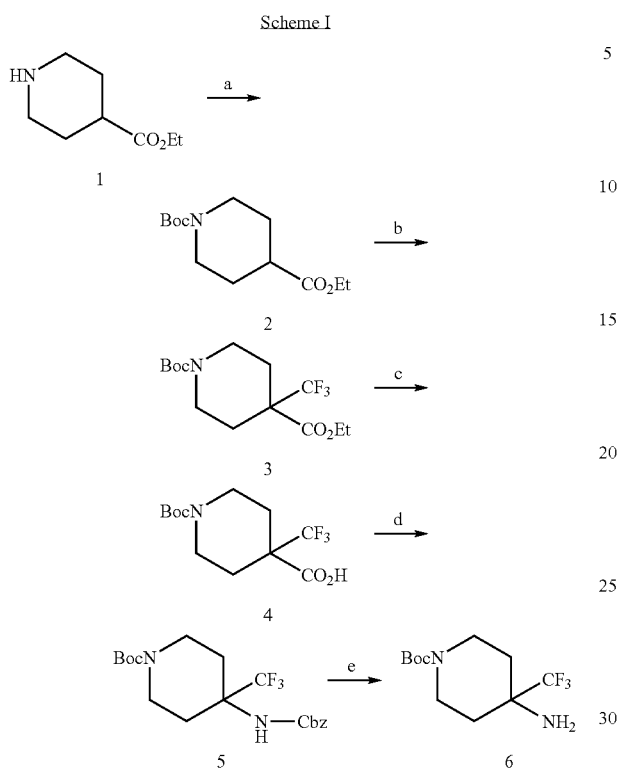

(a) (Boc)$_2$O, CH$_2$Cl$_2$; (b) LDA, then CF$_3$—X; (c) NaOH, H$_2$O, EtOH; (d) DPPA, Et$_3$N, toluene, then BnOH; (e) H$_2$, Pd/C, EtOH.

Commercially-available ethyl isonipecotate (I-1) reacts with an appropriate acylating agent, preferably di-tert-butyl dicarbonate, to afford the protected derivative I-2. Typical solvents for this reaction include CH$_2$Cl$_2$, THF, or DMF. The protecting group for the amine must be compatible with subsequent chemistry, and must be readily removable when desired. Methods for the protection of amines are well-known to those of skill in the art, and are described in standard reference volumes, such as Greene "Protective Groups in Organic Synthesis" (published by Wiley-Interscience). Alkylation of I-2 can be accomplished by reaction with an appropriate base, typically LDA or LiN(TMS)$_2$, in an aprotic solvent, usually THF or DME, followed by trapping of the enolate with an appropriate electrophile, to afford I-3. Trifluoromethyl iodide (CF$_3$I) or S-(trifluoromethyl)dibenzothiophenium trifluoromethanesulfonate are typically preferred as electrophilic trifluoromethylating reagents. The ethyl ester of I-3 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid I-4. Curtius-type rearrangement of I-4 gives an intermediate isocyanate, which typically is not isolated, but rather is reacted in situ with an appropriate alcohol, such as benzyl alcohol, to give I-5. Diphenylphosphoryl azide in the presence of an amine base, generally triethylamine or diisopropylethylamine (Hunig's base), is the preferred reagent combination for effecting the Curtius-type rearrangement of I-4, but more classical conditions, such as formation of the acid chloride, reaction with azide anion, and warming of the acyl azide, can also be used. The benzyloxycarbonyl group in I-5 is removed by hydrogenolysis in the presence of a palladium catalyst, typically palladium on activated charcoal, in a suitable solvent, usually EtOH, MeOH, EtOAc, or mixtures thereof, to give amine I-6.

$R^3$ 2-$CF_3$ may be introduced by the following scheme II:

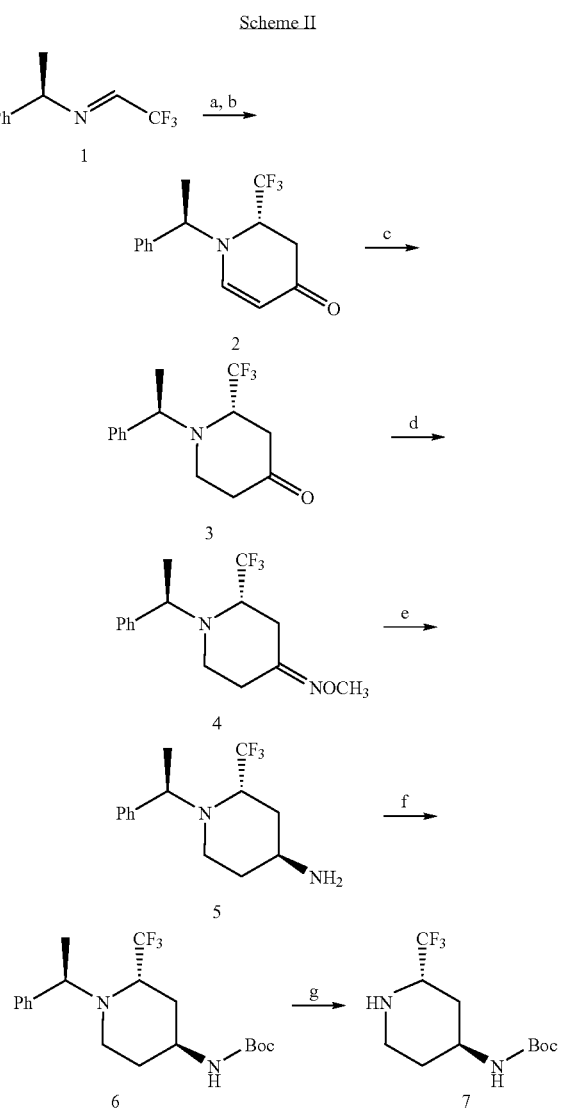

(a) 1-methoxy-3-(trimethylsilyloxy)-1,3-butadiene, ZnCl$_2$, CH$_3$CN; (b) separate diastereomers; (c) L-Selectride® (lithium tri-sec-butylborohydride), THF then pyridinium dichromate, CH$_2$Cl as necessary; (d) NH$_2$OCH$_3$, p-TsOH, toluene; or NH$_2$OCH$_3$, NaOAc, EtOH; (e) LiAlH$_4$, THF; or Al—Ni, 2N NaOH, EtOH; (f) (Boc)$_2$O, CH$_2$Cl$_2$ or THF or DMF; (g) H$_2$, Pd/C, EtOH.

Imine II-1, prepared in standard fashion by acid-catalyzed reaction of trifluoroacetaldehyde ethyl hemiacetal and (R)-(+)-α-methylbenzylamine, reacts with a silyloxydiene, for example 1-methoxy-3-(trimethylsilyloxy)-1,3-butadiene, in a Diels-Alder reaction to afford piperidone II-2. The reaction is conducted in a neutral solvent such as CH$_3$CN, THF, or CH$_2$Cl$_2$, and oftentimes is mediated by a Lewis acid such as ZnCl$_2$. Diastereomers are best separated at this point. The enone II-2 is reduced to the corresponding ketone or alcohol II-3 by reaction with L-Selectride® (lithium tri-sec-butylborohydride) in a suitable solvent, generally THF or DME, followed as necessary by subsequent oxidation of the alcohol to the ketone under standard conditions (pyridinium dichromate) and the ketone is converted to an oxime derivative under standard conditions well-known to those of skill in the art by reaction with O-methylhydroxylamine under standard conditions. Reduction of the oxime derivative under standard conditions (LiAlH$_4$ or according to the general method of Staskun and Van Es (*J. Chem. Soc. C* 1966, 531)) gives a mixture of diastereomeric amines from which the amine II-5 can be isolated. The amine is protected with an appropriate protecting group, preferably a tert-butyl carbamate (see Scheme I), to afford II-6. Typical solvents for this reaction include CH$_2$Cl$_2$, THF, or DMF. The protecting group for the amine must be compatible with subsequent chemistry, and must be readily removable when desired. Methods for the protection of amines are well-known to those of skill in the art, and are described in standard reference volumes, such as Greene "Protective Groups in Organic Synthesis" (published by Wiley-Interscience). The α-methylbenzyl group of II-6 is removed by hydrogenolysis in the presence of a palladium catalyst, typically palladium on activated charcoal, in a suitable solvent, usually EtOH, MeOH, EtOAc, or mixtures thereof, to give amine II-7.

R$^3$ 3-CF$_3$ may be introduced by the following scheme III:

The commercially-available ketone III-1 is converted to the corresponding silyl enol ether III-2 by reaction with a silylating reagent, such a trimethylsilyl chloride or trimethylsilyl triflate, in the presence of an amine base, typically triethylamine, in a suitable solvent, such as diethyl ether, THF, DMF, or mixtures thereof. The silyl enol ether III-2 reacts with an electrophilic trifluoromethylating reagent, such as trifluoromethyl iodide (CF$_3$I) or more preferably S-(trifluoromethyl)dibenzothiophenium trifluoromethanesulfonate (see *Tet. Lett.* 1990, 31, 3579–3582)), in an appropriate solvent, such as THF, DMF, or mixtures thereof, to afford the α-trifluoromethyl ketone III-3. Ketone III-3 reacts with a chiral amine, for instance (R)-(+)-α-methylbenzylamine, under standard acidic catalysis, to afford the imine derivative III-4, which can be reduced to afford amine III-5. This type of reduction is typically conducted using sodium borohydride, sodium cyanoborohydride or sodium (triacetoxy)borohydride, in an F appropriate solvent, such as EtOH, MeOH, THF, CH$_2$Cl$_2$, ClCH$_2$CH$_2$Cl, or mixtures thereof. Diastereomers are best separated at this point. The α-methylbenzyl group of III-5 is removed by hydrogenolysis in the presence of a palladium catalyst, typically palladium on activated charcoal, in a suitable solvent, usually EtOH, MeOH, EtOAc, or mixtures thereof, to give amine III-6.

R$^3$ 2-oxo may be introduced by the following scheme IV:

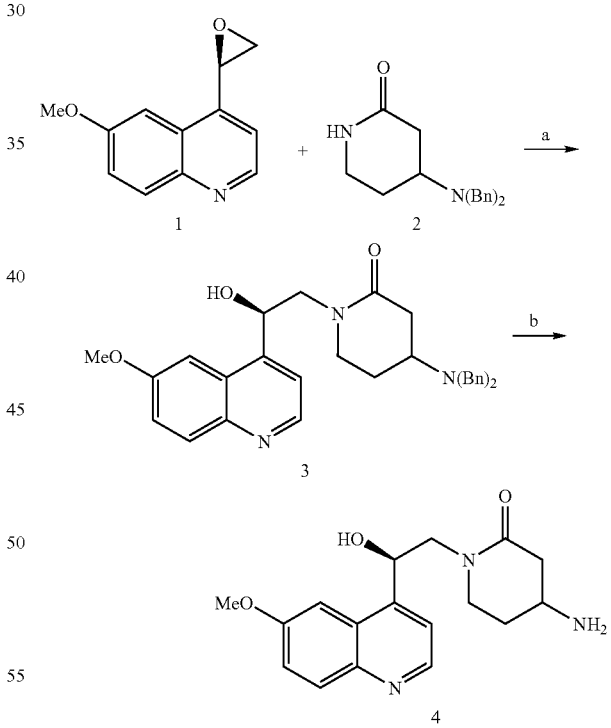

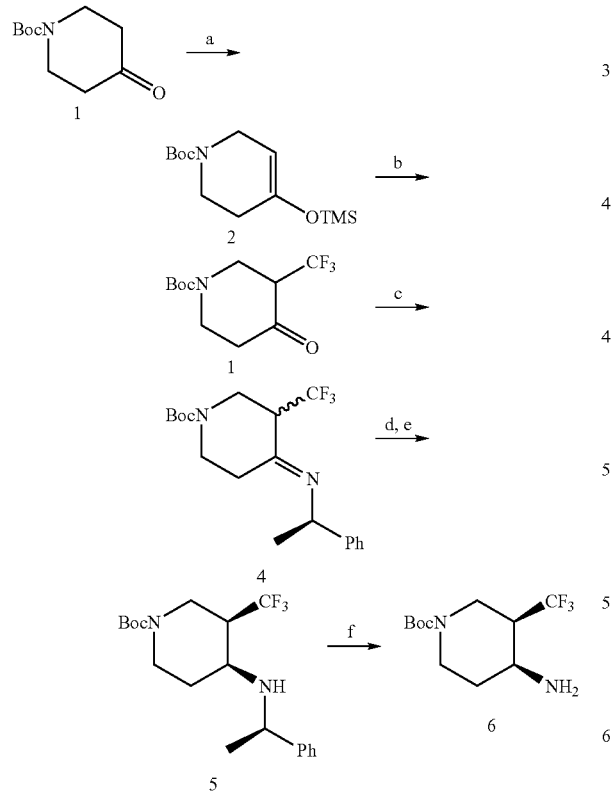

(a) TMSCl, Et$_3$N, DMF; (b) CF$_3$—X, DMF; (c) (R)-(+)-α-methylbenzylamine, p-TsOH, toluene; (d) NaBH$_4$, EtOH; (e) separate diastereomers; (f) H$_2$, Pd/C, EtOH.

(a) NaH, THF, 0° C. to RT; (b) 10% Pd/C, H$_2$, MeOH.

(R,S)-4-(Dibenzylamino)piperidin-2-one (IV-2, Homo-Freidinger Lactam, prepared from (R,S)-aspartic acid according to the procedure of Weber and Gmeiner, *Syntlett*, 1998, 885–887) reacts with an appropriate epoxide, for instance 6-methoxy-4-(R)-oxiranylquinoline (VI-1) or 6-methoxy-4-(R)-oxiranyl-[1,5]naphthyridine, to afford the adduct IV-3. The reaction is mediated by a strong base, preferably sodium hydride, which is used to deprotonate IV-2, and is typically conducted in a polar, aprotic solvent, such as THF, DMF, or mixtures thereof The benzyl groups in IV-3 are removed by hydrogenolysis in the presence of a palladium catalyst, typically palladium on activated charcoal, in a suitable solvent, usually EtOH, MeOH, EtOAc, or mixtures thereof, to give amine IV-4.

$R^3$ 3-F may be introduced by the following scheme V:

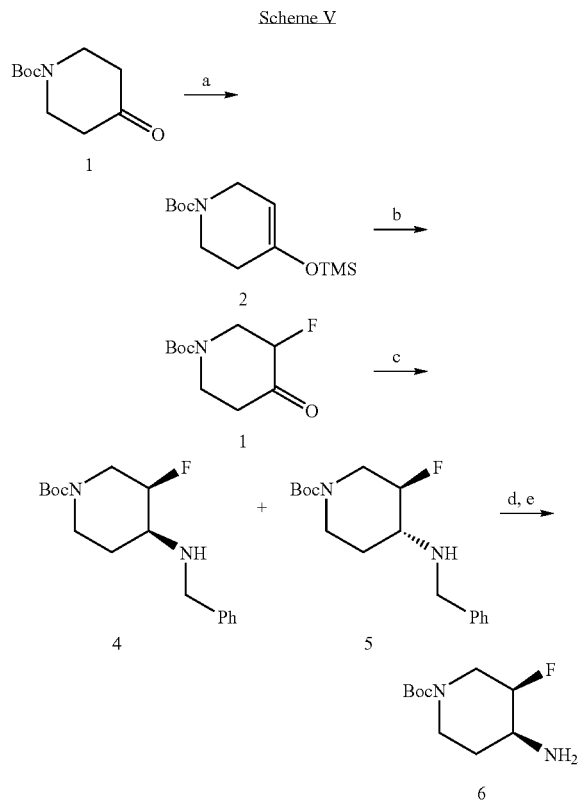

(a) TMSCl, $Et_3N$, DMF, 80° C.; (b) Selectflour, $CH_3CN$; (c) benzylamine, 1,2-dichloroethane, $Na(OAc)_3BH$; (d) separate diastereomers; (e) 10% Pd/C, $H_2$, HCl, EtOH.

The trimethylsilyl enol ether (V-2), prepared from commercially-available N-(tert-butoxycarbonyl)piperidone (V-1) as described in Scheme III, reacts with an electrophilic fluorinating reagent, preferably Selectfluor (1-chloromethyl-4-fluoro-1,4-diazabicyclo[2.2.2]octane bis(tetrafluoroborate), in a neutral solvent such as $CH_3CN$, to afford the α-fluoro ketone V-3. Reductive amination of V-3 with benzylamine according to the procedures described in Schemes I and III gives the expected 4-aminobenzyl-3-fluoro-N-(tert-butoxycarbonyl)piperidine derivatives V-4 and V-5 as a mixture of cis- and trans-isomers in an 8:1 ratio. These diastereomers are separable by chromatography on silica gel. The predominate cis-mixture of enantiomers is debenzylated by catalytic hydrogenation as described in Scheme II, to give the amino derivative V-6.

Other functional groups in $R^3$ may be obtained by conventional conversions of hydroxy, carboxy or cyano groups.

Tetrazoles are conveniently prepared by reaction of sodium azide with the cyano group (e.g. F. Thomas et al, *Bioorg. Med. Chem. Lett.*, 1996, 6(6), 631; K. Kubo et al, *J. Med. Chem.*, 1993, 36, 2182) or by reaction of azidotri-n-butyl stannane with the cyano group followed by acidic hydrolysis (P. L. Ornstein, *J. Org. Chem.*, 1994, 59, 7682 and *J. Med. Chem*, 1996, 39 (11), 2219).

The 3-hydroxy-3-cyclobutene-1,2-dion-4-yl group (e.g. R. M. Soll, *Bioorg. Med. Chem. Lett.*, 1993, 3(4), 757 and W. A. Kinney, *J. Med. Chem.*, 1992, 35(25), 4720) can be prepared by the following sequence: (1) a group $(CH_2)_n$CHO (n=0,1,2) is treated with triethylamine, carbon tetrabromide-triphenylphosphine to give initially $(CH_2)_n$CH=CHBr; (2) dehydrobromination of this intermediate to give the corresponding bromoethyne derivative $(CH_2)_n$C≡CBr (for this 2 stage sequence see D. Grandjean et al, *Tetrahedron Lett.*, 1994, 35(21), 3529); (3) palladium-catalysed coupling of the bromoethyne with 4-(1-methylethoxy)-3-(tri-n-butylstannyl)cyclobut-3-ene-1,2-dione (Liebeskind et al, *J. Org. Chem.*, 1990, 55, 5359); (4) reduction of the ethyne moiety to —$CH_2CH_2$— under standard conditions of hydrogen and palladium on charcoal catalysis (see Howard et al, *Tetrahedron*, 1980, 36, 171); and finally (4) acidic hydrolysis of the methyl ethoxyester to generate the corresponding 3-hydroxy-3-cyclobutene-1,2-dione group (R. M. Soll, *Bioorg. Med. Chem. Lett.*, 1993, 3(4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, *J. Med Chem*, 1996, 39(11), 2232).

The alkyl- and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, *J. Med. Chem.*, 1996, 39(11), 2232).

The hydroxamic acid groups are prepared from the corresponding acids by standard amide coupling reactions e.g. N. R. Patel et al, *Tetrahedron*, 1987, 43(22), 5375.

2,4-Thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitrites is decribed by Y. Kohara et al, *Bioorg. Med. Chem. Lett.*, 1995, 5(17), 1903.

1,2,4-Triazol-5-yl groups may be prepared from the corresponding nitrile by reaction with an alcohol under acid conditions followed by reaction with hydrazine and then an $R^{10}$-substituted activated carboxylic acid (see J. B. Polya in "Comprehensive Heterocyclic Chemistry" Edition 1, p762, Ed A. R. Katritzky and C. W. Rees, Pergamon Press, Oxford, 1984 and J. J. Ares et al, *J. Heterocyclic Chem.*, 1991, 28(5), 1197).

Other substitute on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group or oxidation as appropriate or reaction with an activated acid, isocyanate or alkoxyisocyanate. Primary and secondary hydroxy groups can be oxidised to an aldehyde or ketone respectively and alkylated with a suitable agent such as an organometallic reagent to give a secondary or tertiary alcohol as appropriate. A carboxylate group may be converted to a hydroxymethyl group by reduction of an ester of this acid with a suitable reducing agent such as LiAlH$_4$.

An NH$_2$ substituent on piperidine is converted to NR$^2$R$^4$ by conventional means such as amide or sulphonamide formation with an acyl derivative R$^5$COW or R$^5$SO$_2$W, for compounds where U is CO or SO$_2$ or, where U is CH$_2$, alkylation with an alkyl halide R$^5$CH$_2$-halide in the presence of base, acylation/reduction with an acyl derivative R$^5$COW or reductive alkylation with an aldehyde R$^5$CHO.

Where one of R$^3$ and R$^6$, R$^7$, R$^8$ or R$^9$ contains a carboxy group and the other contains a hydroxy or amino group they may together form a cyclic ester or amide linkage. This linkage may form spontaneously during coupling of the compound of formula (IV) and the piperidine moiety or in the presence of standard peptide coupling agents.

It will be appreciated that under certain circumstances interconversions may interfere, for example, A or B hydroxy groups in A or B and the piperidine substituent NH$_2$ will require protection e.g. as a carboxy- or silyl-ester group for hydroxy and as an acyl derivative for piperidine NH$_2$, during conversion of R$^{1'}$, R$^{2'}$, R$^{3'}$ or R$^{4'}$, or during the coupling of the compounds of formulae (IV) and (V).

Compounds of formulae (IV) and (V) are known compounds, (see for example Smith et al, *J. Amer. Chem. Soc.*, 1946, 68, 1301) or prepared analogously.

Compounds of formula (IV) where X is CR$^6$R$^7$SO$_2$W may be prepared by a route analogous to that of Ahmed El Hadri et al, *J. Heterocyclic Chem.*, 1993, 30(3), 631. Thus compounds of formula (IV) where X is CH$_2$SO$_2$OH may be prepared by reacting the corresponding 4-methyl compound with N-bromosuccinimide, followed by treatment with sodium sulfite. The leaving group W may be converted to another leaving group W, e.g. a halogen group, by conventional methods.

The isocyanate of formula (IV) may be prepared conventionally from a 4-amino derivative such as 4-amino-quinoline, and phosgene, or phosgene equivalent (eg triphosgene) or it may be prepared more conveniently from a 4-carboxylic acid by a "one-pot" Curtius Reaction with diphenyl phosphoryl azide (DPPA) [see T. Shiori et al. *Chem. Pharm. Bull.* 35, 2698–2704 (1987)].

The 4-amino derivatives are commercially available or may be prepared by conventional procedures from a corresponding 4-chloro or 4-trifluoromethanesulphonate derivative by treatment with ammonia (O. G. Backeberg et. al., J. Chem Soc., 381, 1942) or propylamine hydrochloride (R. Radinov et. al., Synthesis, 886, 1986).

4-Alkenyl compounds of formula (IV) may be prepared by conventional procedures from a corresponding 4-halogeno-derivative by e.g. a Heck synthesis as described in e.g. *Organic Reactions*, 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride (POCl$_3$) or phosphorus pentachloride, PCl$_5$. A 4-chloroquinazoline is prepared from the corresponding quinazolin-4-one by reaction with phosphorus oxychloride (POCl$_3$) or phosphorus pentachloride, PCl$_5$. A quinazolinone and quinazolines may be prepared by standard routes as described by T. A. Williamson in *Heterocyclic Compounds*, 6, 324 (1957) Ed. R. C. Elderfield.

Activated carboxy derivatives X=A'COW of formula (IV) may be prepared from X=A'CO$_2$H derivatives in turn prepared from CO$_2$H derivatives by conventional methods such as homologation.

4-Carboxy derivatives of compounds of formula (IV) are commercially available or may be prepared by conventional procedures for preparation of carboxy heteroaromatics well known to those skilled in the art. For example, quinazolines may be prepared by standard routes as described by T. A. Williamson in *Heterocyclic Compounds*, 6, 324 (1957) Ed. R. C. Elderfield. These 4-carboxy derivatives may be activated by conventional means, e.g. by conversion to an acyl halide or anhydride.

Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

A 4-oxirane derivative of compounds of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

Alternatively and preferably, 4-oxirane derivatives can be prepared from bromomethyl ketones which can be obtained from 4-hydroxy compounds by other routes well known to those skilled in the art. For example, hydroxy compounds can be converted to the corresponding 4-trifluoromethanesulphonates by reaction with trirluoromethanesulphonic anhydride under standard conditions (see K. Ritter, Synthesis, 1993, 735). Conversion into the corresponding butyloxyvinyl ethers can be achieved by a Heck reaction with butyl vinyl ether under palladium catalysis according to the procedure of W. Cabri et al, J. Org. Chem, 1992, 57 (5), 1481. (Alternatively, the same intermediates can be attained by Stille coupling of the trifluoromethanesulphonates or the analaogous chloro derivatives with (1-ethoxyvinyl)tributyl tin, T. R. Kelly, J. Org. Chem., 1996, 61, 4623.) The alkyloxyvinyl ethers are then converted into the corresponding bromomethylketones by treatment with N-bromosuccinimide in aqueous tetrahydrofuran in a similar manner to the procedures of J. F. W. Keana, J. Org. Chem., 1983, 48, 3621 and T. R. Kelly, J. Org. Chem., 1996, 61, 4623.

The 4-hydroxyderivatives can be prepared from an aminoaromatic by reaction with methylpropiolate and subsequent cyclisation, analogous to the method described in N. E. Heindel et al, J. Het. Chem., 1969, 6, 77. For example, 5-amino-2-methoxy pyridine can be converted to 4-hydroxy-6-methoxy-[1,5]naphthyridine using this method.

If a chiral reducing agent such as (+) or (−)-B-chlorodiisopinocamphenylborane ['DIP-chloride'] is substituted for sodium borohydride, the prochiral chloromethylketone is converted into the chiral chlorohydrin with ee values generally 85–95% [see C. Bolm et al, *Chem. Ber.* 125, 1169–1190, (1992)]. Recrystallisation of the chiral epoxide gives material in the mother liquor with enhanced optical purity (typically ee 95%).

The (R)-epoxide, when reacted with a piperidine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G. A. Epling and K-Y Lin, *J. Het. Chem.*, 1987, 24, 853–857], or by epoxidation of a 4-vinyl derivative.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5]naphthyridine-3-carboxylic acid, J. T. Adams et al., *J. Amer. Chem. Soc.*, 1946, 68, 1317). A 4-hydroxy-[1,5]naphthyridine can be converted to the 4-chloro derivative by heating in phosphorus oxychloride, or to the 4-methanesulphonyloxy or 4-trifluoromethanesulphonyloxy derivative by reaction with methanesulphonyl chloride or trifluoromethanesulphonic anhydride, respectively, in the presence of an organic base. A 4-amino 1,5-naphthyridine can be obtained from the 4-chloro derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p581–627, Ed A. R. Katritzky and C. W. Rees, Pergamon Press, Oxford, 1984).

The 4-hydroxy and 4-amino-cinnolines may be prepared following methods well known to those skilled in the art [see A. R. Osborn and K. Schofield, *J. Chem. Soc.* 2100 (1955)]. For example, a 2-aminoacetopheneone is diazotised with sodium nitrite and acid to produce the 4-hydroxycinnoline with conversion to chloro and amino derivatives as described for 1,5-naphthyridines.

For compounds of formula (V), suitable amines may be prepared from the corresponding 4-substituted piperidine acid or alcohol. In a first instance, an N-protected piperidine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected piperidine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, *Tetrahedron Lett.*, 1984, 25, 3515). This undergoes cleavage on treatment with tetrabutylammonium fluoride to give the 4-amine substituted N-protected piperidine.

In a second instance, an N-protected piperidine containing an alcohol bearing substituent undergoes a Mitsunobu reaction (for example as reviewed in Mitsunobu, *Synthesis*, (1981), 1), for example with succinimide in the presence of diethyl azodicarboxylate and triphenylphosphine to give the phthalimidoethylpiperidine. Removal of the phthaloyl group, for example by treatment with methylhydrazine, gives the amine of formula (V).

$R^5CH_2$-halides, acyl derivative $R^5COW$ and $R^5SO_2W$ or aldehydes $R^5CHO$ are commercially available or are prepared conventionally. The aldehydes maybe prepared by partial reduction of the $R^5$-ester with lithium aluminium hydride or di-isobutylaluminium hydride or more preferably by reduction to the alcohol, with lithium aluminium hydride or sodium borohydride, followed by oxidation to the aldehyde with manganese (II) dioxide. The aldehydes may also be prepared from carboxylic acids in two stages by conversion to a mixed anhydride for example by reaction with isobutyl chloroformate followed by reduction with sodium borohydride (R. J. Alabaster et al., Synthesis, 598, 1989) to give the hydroxymethyl substituted heteroaromatic or aromatic and then oxidation with a standard oxidising agent such as pyridinium dichromate or manganese (II) dioxide. Acyl derivative $R^5COW$ may be prepared by activation of the $R^5$-acid. $R^5CH_2$-halides such as bromides may be prepared from the alcohol $R^5CH_2OH$ by reaction with phosphorus tribromide in DCM/triethylamine. Alternatively the aldehyde $R^5CHO$ and sulphonic acid derivative $R^5SO_2W$ may be generated by treatment of the $R^5H$ heterocycle with suitable reagents. For example by formylation with hexamine in either trifluoroacetic acid or methanesulfonic acid, in a modified Duff procedure [O. I. Petrov et al. *Collect. Czech. Chem. Commun.* 62, 494–497 (1997)]. Reaction of a $R^5H$ heterocycle with chlorosulphonic acid gives the sulphonic acid derivative (by methods analogous to Techer et. al., *C. R. Hebd. Seances Acad. Sci. Ser.C;* 270, 1601, 1970).

$R^5$ heterocycles are commercially available or may be prepared by conventional methods.

The amines $R^{2'}R^{4'}NH$ are available commercially or prepared conventionally. For example amines $R^5CH_2NH_2$ may be prepared from a bromomethyl derivative by reaction with sodium azide in dimethylformamide (DMF), followed by hydrogenation of the azidomethyl derivative over palladium-carbon. An alternative method is to use potassium phthalimide/DMF to give the phthalimidomethyl derivative, followed by reaction with hydrazine in DCM to liberate the primary amine.

Conversions of $R^{1a'}$, $R^{1'}$, $R^{2'}$, $R^{3'}$ and $R^{4'}$ may be carried out on the intermediates of formulae (IV), and (V) prior to their reaction to produce compounds of formula (I) in the same way as described above for conversions after their reaction.

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial "split and mix" approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable derivatives thereof.

Novel intermediates of formulae (IV) and (V) are also part of this invention.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable derivative thereof is administered in the above-mentioned dosage range.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

EXAMPLES

Example 1

Preparation of 6-[({(3S,4R)-3-fluoro-1-[(R)-2-hydroxy-2-(6-methoxyquinolin-4-yl)-ethyl]piperidin-4-ylamino}methyl)]-[1,2,3]thiadiazolo[5,4-b]pyridine and 6-[({(3R,4S)-3-fluoro-1-[(R)-2-hydroxy-2-(6-methoxyquinolin-4-yl)-ethyl]piperidin-4-ylamino}methyl)]-[1,2,3]thiadiazolo[5,4-b]pyridine

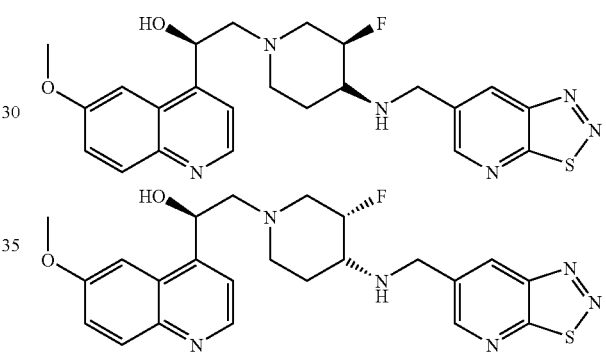

Method A (a) (3R, 4S) and (3S, 4R)-4-Amino-1-tert-butoxycarbonyl-3-fluoropiperidine To a solution of the enantiomeric mixture of cis-4-benzylamino-1-tert-butoxycarbonyl-3-fluoropiperidine (prepared according to the procedures of J. Med. Chem. 1999, 42, 2087–2104, 1.0 g, 3.2 mmole) in EtOH (40 mL) was added 3 N HCl (2.5 mL) and 10% Pd/C (50 mg). The reaction was shaken under $H_2$ (40 psi) on a Parr hydrogenator apparatus for 14 h, then was filtered through celite® filter medium. The filtrate was concentrated under reduced pressure, and the residue was purified by flash chromatography on silica gel (10% MeOH/$CHCl_3$) to afford the title compound (370 mg, 53%) as a white solid: MS (ES) m/e 219 (M+H)$^+$.

(b) [1,2,3]Thiadiazolo[5,4-b]pyridine-6-carboxaldehyde

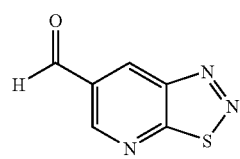

(i) 5-Amino-6-thioxo-1,6-dihydro-pyridine-3-carboxylic acid methyl ester

A mixture of sodium sulfide nonahydrate (2.17 g) and sulfur (0.29 g) was heated in boiling water (20 mL) until the solution was homogeneous and added to a solution of 6-chloro-5-nitro-nicotinic acid methyl ester [prepared as described by A. H. Berrie et al. *J. Clem. Soc.* 2590–2594 (1951)] (3.10 g) in methanol (50 mL). The mixture was boiled for 15 minutes and cooled. The resulting disulfide was collected and washed with water to give a yellow solid (2.46 g). The solid (5 g) in acetic acid (100 mL) and 4M HCl in dioxan (50 mL) was treated with zinc dust (12 g) and the mixture was stirred at room temperature for 30 minutes, filtered and evaporated to dryness. Sodium acetate and sodium sulfate were added and the mixture was extracted with warm chloroform and chromatographed on silica gel, eluting with chloroform then methanol-chloroform to afford a yellow solid (2.3 g).

MS (+ve ion electrospray) m/z 185(MH+)

(ii) [1,2,3]Thiadiazolo[5,4-b]pyridine-6-carboxylic acid methyl ester

The amine (i) (1.3 g) was suspended in 0.5 M hydrochloric acid (200 mL) and cooled to −3° C. A solution of sodium nitrite (487 mg) in water (3 mL) was added dropwise over 10 minutes and the mixture was stirred for 2 hours when the solid product was collected and chromatographed on silica gel (chloroform) to afford a solid (0.90 g)

MS (+ve ion electrospray) m/z 196 (MH+)

(iii) [1,2,3]Thiadiazolo[5,4-b]pyridine-6-carboxylic acid

The ester (ii) (0.94 g) was hydrolysed with aqueous sodium hydroxide in tetrahydrofuran to afford a solid (0.84 g).

MS (−ve ion electrospray) m/z 180 (M−H).

(iv) [1,2,3]Thiadiazolo[5,4-b]pyridin-6-yl-methanol

The carboxylic acid (iii) (0.82 g) was reacted with isobutylchloroformate and sodium borohydride to afford a semisolid (0.12 g), after chromatography on silica gel (chloroform).

(v) [1,2,3]Thiadiazolo[5,4-b]pyridine-6-carboxaldehyde

The alcohol (iv) (0.10 g) was oxidised with manganese dioxide to afford a solid (51 mg).

MS (+ve ion electrospray in methanol) m/z 198 (MH+ for methanol adduct)

(c) (3R,4S) and (3S,4R)-3-Fluoro-4-[([1,2,3]thiadiazolo[5,4-b]pyridine-6-ylmethyl)-amino]-piperidine A solution of cis-4-amino-1-tert-butoxycarbonyl-3-fluoropiperidine (1a) (1.00 mmole) in $CH_2Cl_2$ (5 mL) and EtOH (0.5 mL) is treated with anhydrous $Na_2SO_4$ (280 mg) and [1,2,3]thiadiazolo[5,4-b]pyridine-6-carboxaldehyde (1b) (1.10 mmole). The resulting solution is stirred at room temperature, then sodium triacetoxy borohydride (320 mg, 1.50 mmole) is added. The mixture is quenched by the addition of water (2 mL) and the volatiles removed in vacuo. Purification gives the desired compound.

(d) 6-Methoxyquinoline-4-carboxylic acid

The title compound was prepared by modification of the procedure described by W. E. Doering and J. D. Chanley, *J. Amer. Chem. Soc.*, 1946, 68, 586. A mixture of quinone (derived from quinine by reaction with potassium tert-butoxide and benzophenone in toluene) (225 g, 0.70 mol), tert-butanol (1 litre) and water (10 ml) was treated with potassium tert-butoxide (170 g, 1.5 mol). The mixture was stirred at 30° C., while air was bubbled through for 3 days. The mixture was diluted with diethyl ether and water and the layers separated. The aqueous phase was extracted with ethyl acetate. The combined diethyl ether and ethyl acetate extracts were dried over magnesium sulfate and evaporated to give recovered starting material (approximately 100 g). The aqueous phase was acidified to pH5 with 5M hydrochloric acid. The precipitate was collected by filtration, washed with water and methanol, then dried to give 6-methoxyquinoline-4-carboxylic acid as a yellow solid (64.6 g, 46%).

$^1$H NMR δH (d-6 DMSO) 6.23–5.95 (1H, m), 5.34–5.06 (2H, m), 3.37–2.92 (5H, m), 2.70 (1H, m), 2.38–2.15 (3H, m), 1.94–1.52 (2H, m)

(e) [R]-2-(6-Methoxyquinolin-4-yl)oxirane

A solution of 6-methoxyquinoline-4-carboxylic acid (1d) (10 g) in dichloromethane was heated under reflux with oxalyl chloride (5 ml) and dimethylformamide (2 drops) for 1 hour and evaporated to dryness. The residue, in dichloromethane (100 ml) was treated with a 2M solution of trimethylsilyldiazomethane in hexane (50 ml) and stirred at room temperature for 18 hours. 5M Hydrochloric acid (150 ml) was added and the solution was stirred at room temperature for 3 hours. It was basified with sodium carbonate solution, extracted with ethyl acetate and chromatographed on silica gel eluting with ethyl acetate-hexane to give the chloromethyl ketone (4.2 g). A batch of the chloromethyl ketone (20 g) was reduced with (+)-B-chlorodiisopinocamphenylborane (40 g) in dichloromethane (400 ml) at room temperature for 18 hours followed by treatment with diethanolamine (30 g) for 3 hours. The product was chromatographed on silica gel eluting with ethyl acetate-hexane to give the chloroalcohol (16.8 g), which was dissolved in tetrahydrofuran (100 ml) and reacted with sodium hydroxide (2.6 g) in water (13 ml) for 1.5 hours. The reaction mixture was evaporated to dryness and chromatographed on silica gel eluting with ethyl acetate-hexane to give the title compound as a solid (10.4 g) (84% ee by chiral HPLC). Recrystallisation from ether-pentane gave mother-liquor (7.0 g) (90% ee).

MS (+ve ion electrospray) m/z 202 (MH+)

The absolute stereochemistry was defined to be (R) by an NMR study on the Mosher's esters derived from the product obtained by reaction with 1-t-butylpiperazine.

(f) Title Compounds

To an enantiomeric mixture of 3-fluoro-4-[([1,2,3]thiadiazolo[5,4-b]pyridine-6-ylmethyl)-amino]-piperidine (1c) (0.33 mmole) in DMF (2 mL) is added $LiClO_4$ (0.33 mmole), $K_2CO_3$ (0.66 mmole), and 6-methoxy-4-(R)-oxiranylquinoline (0.33 mmole). The reaction is heated at 90° C. for 18 h, cooled to RT and concentrated under reduced pressure. The residue is partitioned between ethyl acetate and $H_2O$, and the layers are separated. The aqueous phase is further extracted with ethyl acetate, and the combined organic extracts are dried over $MgSO_4$ and concentrated under reduced pressure. The residue is purified by flash chromatography on silica gel to give the title compounds.

Method B (g) (3R, 4S) and (3S, 4R)-4-Benzyloxycarbonylamino-3-fluoropiperidine (3R, 4S) and (3S, 4R)-4-Benzylamino-1-tert-butoxycarbonyl-3-fluoropiperidine [see (1a)] (10.0 g) in methanol (200 mL) was hydrogenated over 20% palladium hydroxide on carbon (2.5 g) at 30 psi for 7 h, then filtered through Celite and evaporated. The crude amine (7.49 g) in DCM (150 mL) and triethylamine (3.5 mL) was treated with benzyl chloroformate (4.0 mL) and the mixture stirred vigorously for 5 h. The organic phase was separated, dried, and evaporated. The product (4.27 g) was dissolved in DCM (40 mL) and stirred with TFA (8 mL) for 4 h then evaporated. The residue was basified with sodium carbonate solution, extracted with 10% methanol in DCM and the extracts dried and evaporated to give a white solid (2.92 g).

(h) (R)-2-(3R, 4S)-(4-Amino-3-fluoropiperidin-1-yl)-1-(6-methoxyquinolin-4-yl)-ethanol and (R)-2-(3S, 4R)-(4-Amino-3-fluoropiperidin-1-yl)-1-(6-methoxyquinolin-4-yl)-ethanol The piperidine (1g) (0.63 g) and 6-methoxy-4-(R)-oxiranylquinoline (1e) (0.5 g) were heated together at 85° C. for 3 h, then allowed to cool, and the product purified on silica gel (methanol-DCM). The material obtained (0.77 g) was dissolved in ethanol (30 mL) and hydrogenated with 10% Pd/C (0.35 g) for 5 h, then filtered through Celite® and evaporated to give a yellow foam (0.459 g)

MS (ES) m/z 320 (M+H)$^+$. MS (APCl$^-$) m/z 195 ([M−H]$^-$, 50%), 165(100%).

(i) Title Compounds

[1,2,3]Thiadiazolo[5,4-b]pyridin-6-yl-methanol (1b)(iv) (30 mg) in dry THF (2 mL) was treated with triethylamine (0.025 mL) and methanesulfonyl chloride (0.014 mL) to form the mesylate. After 1.5 h the mixture was diluted with DMF (2 mL) and potassium carbonate (25 mg) was added followed by the amino-piperidine (1h) ((63 mg) and the mixture was stirred at room temperature for 4 h, then evaporated to dryness. The residue was chromatographed on silica gel (methanol-DCM) to give the free base of the title compound (30 mg) as a 1:1 mixture of isomers.

MS (ES) m/z 469 (M+H)$^+$. $^1$H NMR δH (CDCl$_3$, 250 MHz), 1.80–2.05 (2H, m), 2.28–3.00 (5.5H, m), 3.15–3.30 (1H, m), 3.50 (0.5H, m), 3.91 (3H, s), 4.18 (3H, s and m), 4.90 (1H, d), 5.45 (1H, m), 7.16 (1H, s), 7.38 (1H, dd), 7.62 (1H, t), 8.05 (1H, d), 8.78 (1H, d), 8.88 (1H, d), 8.96 (1H, d).

This material, as a solution in chloroform/methanol, was treated with an excess of 4M HCl in dioxan and evaporated to dryness. The solid was triturated under ether, filtered and dried under vacuum to provide the title compound as the hydrochloride salt.

Example 2

Preparation of 5-[({(3S,4R)-3-fluoro-1-[(R)-2-hydroxy-2-(6-methoxyquinolin-4-yl)-ethyl]piperidin-4-ylamino}methyl)]-benzo[1,2,3]thiadiazole and 5-[({(3R,4S)-3-fluoro-1-[(R)-2-hydroxy-2-(6-methoxyquinolin-4-yl)-ethyl]piperidin-4-ylamino}methyl)]-benzo[1,2,3]thiadiazole

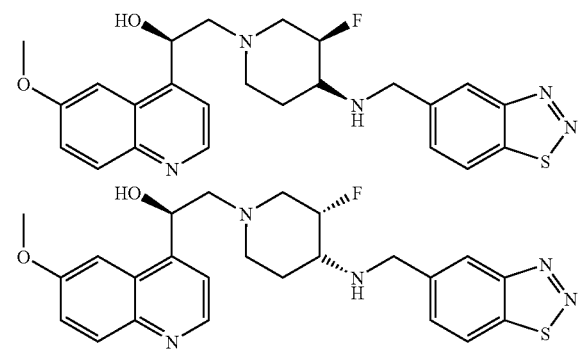

(a) Benzo[1,2,3]thiadiazole-5-carboxaldehyde

Methyl benzo[1,2,3]thiadiazole-5-carboxylate (0.291 g) in THF (2 ml) was treated dropwise with lithium aluminium hydride (1M in THF, 0.71 ml) at 0° C.

After 1.5 h, additional lithium aluminium hydride (0.1 ml) was added. After 0.5 h the mixture was treated with 8% sodium hydroxide, ethyl acetate and sodium sulphate, filtered and evaporated. The resulting crude alcohol was dissolved in dichloromethane (3 ml) and stirred with manganese (II) oxide overnight. Filtration and evaporation of solvent gave the aldehyde.

(b) Title Compounds

These were prepared from amine (1h) (0.054 g) and aldehyde (2a) (0.028 g) in DMF (5 ml) with sodium triacetoxyborohydride (0.16 g) at room temperature for 4.5 hr. The reaction mixture was quenched with dilute HCl, basified with sodium carbonate and evaporated. The residue was diluted with water and extracted with 10% methanol in chloroform, dried (sodium sulfate), evaporated and chromatographed on silica gel (methanol-DCM) to afford the title compound as the free base (9 mg).

LC/MS (ES) m/z 468 (M+H)$^+$. $^1$H NMR δH (CDCl$_3$, 400 MHz), 1.70–2.00 (2H, m), 2.20–3.60 (7H, m), 3.93 (3H, s), 4.14 (2H, s), 4.30 (1H, br s), 4.89 (1H, dd), 5.43 (1H, m), 7.19 (1H, s), 7.63 (1H, m), 7.75 (1H, dd), 8.04 (2H, m), 8.62 (1H, s), 8.76 (1H, d).

This material, as a solution in chloroform/methanol, was treated with an excess of 4M HCl in dioxan and evaporated to dryness. The solid was triturated under ether, filtered and dried under vacuum to provide the title compound as the hydrochloride salt.

Example 3

Preparation of {3-Fluoro-1-[(R)-2-hydroxy-2-(6-methoxy-[1,5]naphthyridin-4-yl)-ethyl]-piperidin-4-yl}-[1,2,3]thiadiazolo[5,4-b]pyridin-6-ylmethyl-amine Diastereoisomer 1 Dihydrochloride

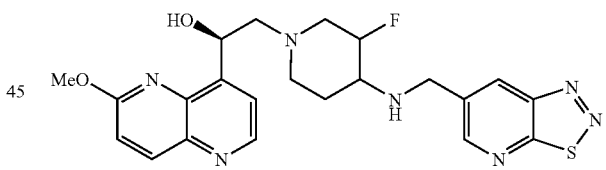

(a) 4-Hydroxy-6-methoxy-[1,5]-naphthyridine

5-Amino-2-methoxypyridine (55 g, 0.44 mol) in methanol (1000 ml) with methyl propiolate (40 ml, 0.44 mol) was stirred for 48 hours, then evaporated and the product purified by chromatography on silica gel (dichloromethane) followed by recrystallisation from dichloromethane-hexane (44.6 g, 48%).

The unsaturated ester (10.5 g, 0.05 mol) in warm Dowtherm A (50 ml) was added over 3 minutes to refluxing Dowtherm A, and after a further 20 minutes at reflux the mixture was cooled and poured into ether. The precipate was filtered to give a solid (6.26 g, 70%)

(b) Bromomethyl-(6-methoxy-[1,5]-naphthyridin-4-yl)-ketone

The naphthyridine (3a) (10 g, 0.057 mol) in dichloromethane (200 ml) containing 2,6-lutidine (9.94 ml, 0.086 mol) and 4-dimethylaminopyridine (0.07 g, 0.0057 mol) was cooled in ice and treated with trifluoromethanesulfonic anhydride (10.5 ml, 0.063 mol). After stirring for 2.5 hours the mixture was washed with saturated ammonium chloride solution, dried, evaporated and purified on silica (dichloromethane). The triflate (13.2 g, 0.044 mol) in DMF (200 ml) with triethylamine (12 ml, 0.086 mol) butyl vinyl ether (22 ml, 0.17 mol), palladium (II) acetate (0.97 g, 0.0044 mol) and 1,3-bis(diphenylphosphino)propane (1.77 g, 0.0044 mol) was heated at 60° C. for 3 hours then evaporated and chromatographed on silica gel (dichloromethane) to give a yellow solid (10.7 g, 95%). This was dissolved in THF (250 ml) and water (40 ml) and treated with N-bromosuccinimide (7.4 g, 0.042 mol) for 1 hour, then evaporated and chromatographed on silica gel (dichloromethane) to give the ketone (10.42 g, 98%).

(c) (R)-2-Bromo-1-(6-methoxy-[1,5]-naphthyridin-4-yl)ethanol

The ketone (3b) (6.6 g, 0.023 mol) in toluene was treated with (+)-B-chlorodiisopinocamphenylborane ((+)-DIP-chloride) (12 g, 0.037 mol) and stirred overnight, then diethanolamine (15 g, 0.14 mol) was added and the mixture stirred for 3 hours, filtered and evaporated. Chromatography on silica gel (ethyl acetate-hexane)gave a white solid (4.73 g, 73%).

(d) (R)-2-(6-Methoxy-[1,5]-naphthyridin-4-yl)oxirane

The alcohol (3c) (4.8 g, 0.017 mol) in methanol (20ml) was stirred with potassium carbonate (2.6 g, 0.019 mol) for 1 hour, then evaporated and chromatographed on silica gel (ethyl acetate-hexane-dichloromethane) to give a solid (3.14 g, 92%), (Batches typically >90% ee by chiral HPLC).

MS (+ve ion electrospray) m/z 203 (MH+).

(e) cis-4-Benzylamino-1-tert-butoxycarbonyl-3-fluoropiperidine

4-Benzylamino-1-tert-butoxycarbonyl-3-fluoropiperidine was prepared according to the procedures of *J. Med. Chem.* 1999, 42, 2087–2104 as a mixture of isomers (approx 8:1 cis:trans, 29.8 g, 0.096 mole). The mixture was dissolved in DCM, extracted with 0.2M HCl, basified with $Na_2CO_3$ solution, extracted with DCM and chromatographed on silica gel to give the cis-isomer in the later fractions (15.6 g, 52%). Combined batches (32 g, 0.103 mole) were separated by preparative HPLC on a Chiralpak AD column eluting with hexane:ethanol (9:1) to give faster running enantiomer [Enantiomer 1] (15.0 g, 47%, 99% ee) $[\alpha]_D$+40.5° and slower running enantiomer [Enantiomer 2] (15.0 g, 47%, 97%ee) $[\alpha]_D$−39.5°.

(f) 4-Benzyloxycarbonylamino-3-fluoropiperidine Enantiomer 1 cis-(+)-4-Benzylamino-1-tert-butoxycarbonyl-3-fluoropiperidine [(3e); Enantiomer 1] (15.0 g, 0.049 mole) in ethanol (300 ml) was hydrogenated over 20% palladium hydroxide on carbon (4g) at 30 psi for 5 h, then filtered through Celite® and evaporated. The crude amine was dissolved in ethyl acetate (100 mL), saturated sodium hydrogen carbonate solution (100 mL) was added followed by benzyl chloroformate (7.6 mL, 0.53 mole)and the mixture stirred vigorously for 4 h. The organic phase was separated dried and evaporated. The product was dissolved in DCM (75 mL) and stirred with TFA (20 mL) for 4 h then evaporated. The residue was basified with sodium carbonate solution, extracted with 10% methanol in DCM and the extracts dried and evaporated to give a white solid (12.1 g, 98%), $[\alpha]_D$+ 61.1° (MeOH).

(g) (R)-2-(4-Amino-3-fluoropiperidin-1-yl)-1-(6-methoxy-[1,5]naphthyridin-4-yl)-ethanol Diastercoisomer 1

4-Benzyloxycarbonylamino-3-fluoropiperidine Enantiomer 1 (3f) (2.49 g) and (R)-2-(6-Methoxy-[1,5]-naphthyridin-4-yl)oxirane (3d) (100% ee) (2.0 g) were heated together at 80–88° C. for 2.5 h with 2 drops of DMF, then allowed to cool, and the product purified on silica gel (methanol-DCM) to give a solid (3.88 g). The material was dissolved in ethanol (40 mL), 1,4-cyclohexadiene (7.7 mL) was added and the solution was stirred at room temperature with 10% Pd/C (3.5 g) for 2 h, then filtered through Celite® and evaporated to give a foam (2.53 g).

LC/MS (ES) m/z 321 (M+H)+.

(h) Title Compound

The free base of the title compound was prepared from amine (3g) and [1,2,3]thiadiazolo[5,4-b]pyridin-6-yl-methanol (1b)(iv) by the method of Example (1i) (41%).

LC/MS (ES) m/z 470 (M+H)+.

$^1$H NMR δH (CDCl$_3$, 250 MHz), 1.85–2.00 (2H, m), 2.28–3.00 (4H, m), 3.15 (1H, dd), 3.52 (1H, m), 4.02 (3H, s), 4.17 (2H, s), 4.30 (1H, br s), 4.90 (1H, d), 5.70 (1H, m), 7.12 (1H, d), 7.80 (1H, d), 8.23 (1H, d), 8.78 (1H, d), 8.88 (1H, d), 8.96 (1H, d).

This material, as a solution in chloroform/methanol, was treated with an excess of 4M HCl in dioxan and evaporated to dryness. The solid was triturated under ether, filtered and dried under vacuum to provide the title compound.

DCM=dichloromethane
DMF=dimethylformamide
THF=tetrahydrofuran

Biological Activity

The MIC (μg/ml) of test compounds against various organisms may be determined: *S. epidermidis* CL7, *S. aureus* WCUH29, *S. pneumoniae* 1629, *S. pyogenes* CN10, *H. influenzae* ATCC49247, *E.faecalis* 2, *E. faecium* 8, *M. catarrhalis* Ravisio, *E. coli* 7623.

Compounds of Examples 1 and 3 have MIC's in the range 0.06–16 μg/ml versus all of these organisms.

The invention claimed is:

1. A compound of formula (I) or a pharmaceutically acceptable derivative thereof:

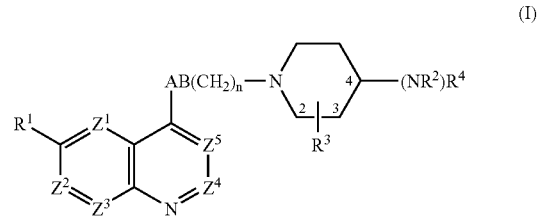

(I)

wherein:
one of $Z^1$, $Z^2$, $Z^3$, $Z^4$ and $Z^5$ is N, one is $CR^{1a}$ and the remainder are CH, or one or two of $Z^1$, $Z^2$, $Z^3$, $Z^4$ and $Z^5$ are independently $CR^{1a}$ and the remainder are CH;

$R^1$ and $R^{1a}$ are independently hydrogen; hydroxy; $(C_{1-6})$ alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$ alkylthio, heterocyclylthio, heterocyclyloxy, arylthio, aryloxy, acylthio, acyloxy or $(C_{1-6})$ alkylsulphonyloxy; $(C_{1-6})$alkoxy-substituted$(C_{1-6})$alkyl; halogen; $(C_{1-6})$ alkyl; $(C_{1-6})$ alkylthio; trifluoromethyl; trifluoromethoxy; nitro; azido; acyl; acyloxy; acylthio; $(C_{1-6})$ alkylsulphonyl; $(C_{1-6})$alkylsulphoxide; arylsulphonyl;

arylsulphoxide or an amino, piperidyl, guanidino or amidino group optionally N-substituted by one or two $(C_{1-6})$alkyl, acyl or $(C_{1-6})$ alkylsulphonyl groups;

or when $Z^5$ is $CR^{1a}$, $R^{1a}$ may instead be cyano, hydroxymethyl or carboxy;

or $R^1$ and $R^{1a}$ on adjacent positions may together form ethylenedioxy;

provided that when $Z^1$, $Z^2$, $Z^3$, $Z^4$ and $Z^5$ are $CR^{1a}$ or CH, then $R^1$ is not hydrogen;

$R^2$ is hydrogen, or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$ alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy $(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$ alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$ alkenyloxycarbonyl, $(C_{2-4})$alkenylcarbonyl; oxo; $(C_{1-4})$ alkylsulphonyl; $(C_{2-4})$ alkenylsulphonyl; or $(C_{1-4})$aminosulphonyl wherein the amino group is optionally substituted by $(C_{1-4})$alkyl or $(C_{2-4})$alkenyl;

$R^3$ is in the 2-, 3- or 4-position and is trifluoromethyl or is in the 2-position and is oxo; or $R^3$ is in the 3-position and is fluorine or amino wherein the amino group is optionally substituted by: hydroxy; $(C_{1-6})$alkylsulphonyl; trifluoromethylsulphonyl; $(C_{2-6})$ alkenylsulphonyl; $(C_{1-6})$alkylcarbonyl; $(C_{2-6})$alkenylcarbonyl; $(C_{1-6})$ alkoxycarbonyl; $(C_{2-6})$ alkenyloxycarbonyl; $(C_{1-6})$ alkyl; or $(C_{2-6})$alkenyl; wherein a $(C_{1-6})$alkyl or $(C_{2-6})$ alkenyl moiety may be optionally substituted with up to 2 groups $R^{12}$ independently selected from: halogen; $(C_{1-6})$alkylthio; trifluoromethyl; cyano; carboxy; tetrazolyl; 2-oxo-oxazolidinyl; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; $(C_{1-6})$ alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkylcarbonyl, $(C_{2-6})$ alkenylcarbonyl or aminocarbonyl wherein the amino group is optionally substituted by $(C_{1-6})$alkyl, $(C_{2-6})$alkenyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$ alkenylcarbonyl, $(C_{1-6})$alkyl, $(C_{2-6})$ alkenyl, $(C_{1-6})$ alkylsulphonyl, $(C_{2-6})$alkenylsulphonyl or aminocarbonyl wherein the amino group is optionally substituted by $(C_{1-6})$alkyl or $(C_{2-6})$alkenyl; in addition when $R^3$ is disubstituted with a hydroxy or amino containing substituent and carboxy containing substituent these may together form a cyclic ester or amide linkage, respectively;

$R^4$ is a group —U—$R^5$ where

U is selected from CO, $SO_2$ and $CH_2$ and $R^5$ is an optionally substituted bicyclic carbocyclic or heterocyclic ring system (A):

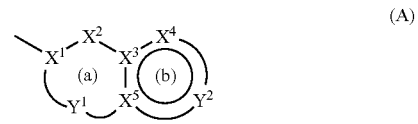

containing up to four heteroatoms in each ring in which ring (a) is aromatic or non aromatic;

$X^1$ is C when part of an aromatic ring or $CR^{14}$ when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^4$ is N, $NR^{13}$, O, $S(O)_x$, CO or $CR^{14}$;

$X^3$ and $X^5$ are independently N or C;

$Y^1$ is a 1 to 3 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring, $Y^2$ is a 2 or 3 atom linker group completing an aromatic ring, each atom of $Y^2$ being independently selected from N, $NR^{13}$, O, $S(O)_x$, CO and $CR^{14}$;

each of $R^{14}$ and $R^{15}$ is independently selected from: H; $(C_{1-4})$alkylthio; halo; carboxy$(C_{1-4})$alkyl; halo$(C_{1-4})$ alkoxy; halo$(C_{1-4})$alkyl; $(C_{1-4})$alkyl; $(C_{2-4})$alkenyl; $(C_{1-4})$ alkoxycarbonyl; formyl; $(C_{1-4})$alkylcarbonyl; $(C_{2-4})$alkenyloxycarbonyl; $(C_{2-4})$ alkenylcarbonyl; $(C_{1-4})$alkylcarbonyloxy; $(C_{1-4})$alkoxycarbonyl$(C_{1-4})$ alkyl; hydroxy; hydroxy$(C_{1-4})$alkyl; mercapto$(C_{1-4})$ alkyl; $(C_{1-4})$alkoxy; nitro; cyano; carboxy; amino or aminocarbonyl optionally substituted as for corresponding substituents in $R^3$; $(C_{1-4})$ alkylsulphonyl; $(C_{2-4})$alkenylsulphonyl; or aminosulphonyl wherein the amino group is optionally mono- or di-substituted by $(C_{1-4})$alkyl or $(C_{2-4})$alkenyl; aryl; aryl $(C_{1-4})$alkyl; aryl$(C_{1-4})$alkoxy or $R^{14}$ and $R^{15}$ may together represent oxo;

each $R^{13}$ is independently H; trifluoromethyl; $(C_{1-4})$ alkyl optionally substituted by hydroxy, $(C_{1-6})$ alkoxy, $(C_{1-6})$alkylthio, carboxy, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$ alkenylcarbonyl, $(C_{1-4})$alkyl or $(C_{2-4})$alkenyl and optionally further substituted by $(C_{1-4})$ alkyl or $(C_{2-4})$alkenyl;

n is 0 or 1;

each x is independently 0, 1 or 2

A is $NR^{11}$, O or $CR^6R^7$ and B is $NR^{11}$, O, $SO_2$ or $CR^8R^9$ and wherein:

each of $R^6$, $R^7$, $R^8$ and $R^9$ is independently selected from: hydrogen; $(C_{1-6})$alkoxy; $(C_{1-6})$ alkylthio; halo; trifluoromethyl; azido; $(C_{1-6})$alkyl; $(C_{2-6})$alkenyl; $(C_{1-6})$ alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$ alkylsulphonyl; $(C_{2-6})$alkenylsulphonyl; or aminosulphonyl wherein the amino group is optionally substituted by $(C_{1-6})$alkyl or $(C_{2-6})$alkenyl; or when n=1 $R^6$ and $R^8$ together represent a bond and $R^7$ and $R^9$ are as above defined; or $R^6$ and $R^7$ or $R^8$ and $R^9$ together represent oxo;

provided that:
when A is $NR^{11}$, B is not $NR^{11}$ or O;
when A is CO, B is not CO, O or $SO_2$;
when n is 0 and A is $NR^{11}$, $CR^8R^9$ can only be CO;
when A is $CR^6R^7$ and B is $SO_2$, n is 0;
when n is 0, B is not $NR^{11}$ or O or $R^8$ and $R^9$ are not optionally substituted hydroxy or amino;
when A is O, B is not $NR^{11}$, O, $SO_2$ or CO and n=1; and
when A-B is $CR^7=CR^9$, n is 1

$R^{10}$ is selected from $(C_{1-4})$alkyl; $(C_{2-4})$alkenyl and aryl any of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$ alkyl or $(C_{2-6})$alkenyl; $(C_{1-6})$alkylsulphonyl; trifluoromethylsulphonyl $(C_{2-6})$ alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl; and $R^{11}$ is hydrogen; trifluoromethyl, $(C_{1-6})$alkyl; $(C_{2-6})$alkenyl; $(C_{1-6})$alkoxycarbonyl; $(C_{1-6})$ alkylcarbonyl; or aminocarbonyl wherein the amino group is optionally substituted by $(C_{1-6})$ alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$ alkenyl;

or where one of $R^3$ and $R^6$, $R^7$, $R^8$ or $R^9$ contains a carboxy group and the other contains a hydroxy or amino group they may together form a cyclic ester or amide linkage.

2. A compound according to claim 1 wherein $Z^5$ is CH, C—Cl or N, $Z^3$ is CH or CF and $Z^1$, $Z^2$ and $Z^4$ are each CH, or $Z^1$ is N, $Z^3$ is CH and $Z^2$ and $Z^4$ are each CH and $Z^5$ is CH or C—Cl.

3. A compound according to claim 1 wherein $R^1$ is methoxy and $R^{1a}$ is H or when $Z^3$ is $CR^{1a}$ it may be C—F or when $Z^5$ is $CR^{1a}$ it may be C—F or C—Cl.

4. A compound according to claim 1 wherein $R^2$ is hydrogen, carboxymethyl, hydroxyethyl, aminocarbonylmethyl, ethoxycarbonylmethyl, ethoxycarbonylallyl or carboxyallyl.

5. A compound according to claim 1 wherein $R^3$ is $CF_3$, fluoro, oxo or amino unsubstituted or substituted by $(C_{1-6})$ alkyl or $(C_{2-6})$alkenyl.

6. A compound according to claim 1 wherein n is 0, A-B is CHOH—$CH_2$, $NR^{11}$—$CH_2$, $NR^{11}$—CO or $CH_2$—$CH_2$ and $R^{11}$ is hydrogen or $(C_{1-4})$alkyl.

7. A compound according to claim 1 wherein U is $CH_2$ and $R^5$ is an aromatic heterocyclic ring (A) having 1–4 heteroatoms of which one is N or $NR^{13}$, $R^{13}$ is H if in ring (a) or in addition $(C_{1-4})$alkyl if in ring (b), $R^{14}$ and $R^{15}$ are independently selected from hydrogen, halo, hydroxy, $(C_{1-4})$alkyl, $(C_{1-4})$alkoxy, trifluoromethoxy, nitro, cyano, aryl$(C_{1-4})$alkoxy and $(C_{1-4})$alkylsulphonyl.

8. A compound according to claim 1 wherein $R^5$ is 4,6-difluoro-indol-2-yl, 1H-pyrrolo[2,3-b]-pyridin-2-yl, 1H-pyrrolo[3,2-b]-pyridin-2-yl, 8-hydroxy-quinolin-2-yl, quinoxalin-2-yl, benzimidazol-2-yl, benzo[1,2,3]-thiadiazol-5-yl, benzothiophen-5-yl, 4,6-difluoro-1H-benzimidazol-2-yl, benzothiazole-5-yl, 3-(R)-2,3-dihydro-[1,4]dioxino[2,3-b]pyridin-3-yl or [1,2,3]thiadiazolo[5,4-b]pyridin-6-yl.

9. A compound according to claim 1 selected from:
6-[({(3S,4R)-3-fluoro-1-[(R)-2-hydroxy-2-(6-methoxyquinolin-4-yl)-ethyl]piperidin-4-ylamino}methyl)]-[1,2,3]thiadiazolo[5,4-b]pyridine and 6-[({(3R,4S)-3-fluoro-1-[(R)-2-hydroxy-2-(6-methoxyquinolin-4-yl)-ethyl]piperidin-4-ylamino}methyl)]-[1,2,3]thiadiazolo[5,4-b]pyridine;
5-[({(3S,4R)-3-fluoro-1-[(R)-2-hydroxy-2-(6-methoxyquinolin-4-yl)-ehtyl]piperidin-4-ylamino}methyl)]-benzo[1,2,3]thiadiazole and 5-[({(3R,4S)-3-fluoro-1-[(R)-2-hydroxy-2-(6-methoxyquinolin-4-yl)-ethyl]piperidin-4-ylamino}methyl)]-benzo[1,2,3]thiadiazole;
{3-Fluoro-1-[(R)-2-hydroxy-2-(6-methoxy-[1,5]naphthyridin-4-yl)-ethyl]-piperidin-4-yl}-[1,2,3]thiadiazolo[5,4-b]pyridin-6-ylmethyl-amine Diastereoisomer 1;
or a pharmaceutically acceptable derivative thereof.

10. A method of treatment of bacterial infections in mammals, particularly in man, which method comprises the administration to a mammal in need of such treatment an effective amount of a compound according to claim 1.

11. A pharmaceutical composition comprising a compound according to claim 1, and a pharmaceutically acceptable carrier.

12. A process for preparing compounds according to claim 1, which process comprises:
reacting a compound of formula (IV) with a compound of formula (V):

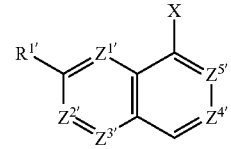

(IV)

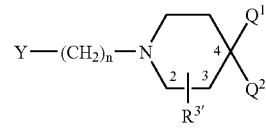

(V)

wherein n is as defined in formula (I); $Z^{1'}$, $Z^{2'}$, $Z^{3'}$, $Z^{4'}$, $Z^{5'}$, $R^{1'}$ and $R^{3'}$ are $Z^1$, $Z^2$, $Z^3$, $Z^4$, $Z^5$, $R^1$ and $R^3$ as defined in formula (I) or groups convertible thereto;

$Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

and X and Y may be the following combinations:
(i) X is A'-COW, Y is H and n is 0;
(ii) X is $CR^6=CR^8R^9$, Y is H and n is 0;
(iii) X is oxirane, Y is H and n is 0;
(iv) X is N=C=O and Y is H and n is 0;
(v) one of X and Y is $CO_2R^y$ and the other is $CH_2CO_2R^x$;
(vi) X is $CHR^6R^7$ and Y is C(=O)$R^9$;
(vii) X is $CR^7=PR^z_3$ and Y is C(=O)$R^9$ and n=1;
(viii) X is C(=O)$R^7$ and Y is $CR^9=PR^z_3$ and n=1;
(ix) Y is COW and X is $NHR^{11'}$ or $NR^{11'}$COW and n=0 or 1 or when n=1 X is COW and Y is $NHR^{11'}$ or $NR^{11'}$COW;
(x) X is C(O=)$R^6$ and Y is $NHR^{11'}$ or X is $NHR^{11'}$ and Y is C(=O)$R^8$ and n=1;
(xi) X is $NHR^{11'}$ and Y is $CR^8R^9W$ and n=1;
(xii) X is $CR^6R^7W$ and Y is $NHR^{11'}$ or OH and n=1;

(xiii) X is $CR^6R^7SO_2W$ and Y is H and n=0;
(xiv) X is W or OH and Y is $CH_2OH$ and n=1;
(xv) X is $NHR^{11'}$ and Y is $SO_2W$ or X is $NR^{11'}SO_2W$ and Y is H, and n=0;
(xvi) X is $NR^{11'}COCH_2W$ or $NR^{11'}SO_2CH_2W$ and Y is H and n=0;
(xvii) X is W and Y is $CONHR^{11'}$;
in which W is a leaving group, e.g. halo or imidazolyl; $R^x$ and $R^y$ are $(C_{1-6})$alkyl; $R^z$ is aryl or $(C_{1-6})$alkyl; A' and $NR^{11'}$ are A and $NR^{11}$ as defined in formula (I), or groups convertible thereto; and oxirane is:

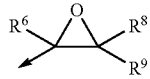

wherein $R^6$, $R^8$ and $R^9$ are as defined in formula (I);

and thereafter optionally or as necessary converting $Q^1$ and $Q^2$ to $NR^2R^4$; converting A', $Z^{1'}$, $Z^{2'}$, $Z^{3'}$, $Z^{4'}$, $Z^{5'}$, $R^{1'}$, $R^{2'}$, $R^{3'}$, $R^{4'}$ and $NR^{11'}$ to A, $Z^1$, $Z^2$, $Z^3$, $Z^4$, $Z^5$, $R^1$, $R^2$, $R^3$, $R^4$ and $NR^{11}$; converting A-B to other A-B, interconverting $R^1$, $R^2$, $R^3$ and/or $R^4$, and/or forming a pharmaceutically acceptable derivative thereof.

13. A compound according to claim 5 wherein $R^3$ is fluoro.

14. A compound according to claim 13 wherein $R^3$ is fluoro in the 3- or 4-position.

15. A compound according to claim 14 wherein $R^3$ is 3-fluoro.

16. A compound according to claim 15 wherein the 3-fluoro is cis to $(NR^2)R^4$.

* * * * *